United States Patent
Smith

(10) Patent No.: US 10,633,320 B2
(45) Date of Patent: Apr. 28, 2020

(54) UPGRADING FUSEL OIL MIXTURES OVER HETEROGENEOUS CATALYSTS TO HIGHER VALUE RENEWABLE CHEMICALS

(71) Applicant: Gevo, Inc., Englewood, CO (US)

(72) Inventor: Jonathan O. Smith, Highlands Ranch, CO (US)

(73) Assignee: Gevo, Inc., Englewood, CO (US)

( * ) Notice: Subject to any disclaimer, the term of this patent is extended or adjusted under 35 U.S.C. 154(b) by 0 days.

(21) Appl. No.: 16/240,542

(22) Filed: Jan. 4, 2019

(65) Prior Publication Data

US 2019/0308922 A1 Oct. 10, 2019

Related U.S. Application Data

(60) Provisional application No. 62/613,740, filed on Jan. 4, 2018, provisional application No. 62/643,103, filed on Mar. 14, 2018, provisional application No. 62/651,534, filed on Apr. 2, 2018, provisional application No. 62/695,685, filed on Jul. 9, 2018, provisional application No. 62/696,220, filed on Jul. 10, 2018, provisional application No. 62/732,749, filed on Sep. 18, 2018, provisional application No. 62/755,307, filed on Nov. 2, 2018.

(51) Int. Cl.

| C07C 45/00 | (2006.01) |
|---|---|
| C07C 1/24 | (2006.01) |
| B01J 23/00 | (2006.01) |
| C07C 45/29 | (2006.01) |
| B01J 23/04 | (2006.01) |
| B01J 23/06 | (2006.01) |
| B01J 23/20 | (2006.01) |
| B01J 23/34 | (2006.01) |
| B01J 29/40 | (2006.01) |
| B01J 37/02 | (2006.01) |
| B01J 37/08 | (2006.01) |
| B01J 21/06 | (2006.01) |
| B01J 37/28 | (2006.01) |
| C07C 27/00 | (2006.01) |
| C07C 67/00 | (2006.01) |
| B01J 21/04 | (2006.01) |
| C08F 236/00 | (2006.01) |
| C08F 236/08 | (2006.01) |

(52) U.S. Cl.
CPC ............. *C07C 45/298* (2013.01); *B01J 21/04* (2013.01); *B01J 21/066* (2013.01); *B01J 23/002* (2013.01); *B01J 23/04* (2013.01); *B01J 23/06* (2013.01); *B01J 23/20* (2013.01); *B01J 23/34* (2013.01); *B01J 29/40* (2013.01); *B01J 37/0201* (2013.01); *B01J 37/0236* (2013.01); *B01J 37/08* (2013.01); *B01J 37/28* (2013.01); *C07C 1/24* (2013.01); *C07C 27/00* (2013.01); *C07C 45/002* (2013.01); *C07C 67/00* (2013.01); *C08F 236/00* (2013.01); *C08F 236/08* (2013.01); *B01J 2523/00* (2013.01); *C07C 2521/02* (2013.01); *C07C 2521/04* (2013.01); *C07C 2521/06* (2013.01); *C07C 2521/10* (2013.01); *C07C 2523/06* (2013.01); *C07C 2523/34* (2013.01); *C07C 2527/18* (2013.01); *C07C 2527/195* (2013.01); *C07C 2529/40* (2013.01)

(58) Field of Classification Search
CPC ........ C07C 45/298; C07C 1/24; B01J 23/002; B01J 23/04; B01J 23/39; B01J 23/06
See application file for complete search history.

(56) References Cited

U.S. PATENT DOCUMENTS

| 1,033,180 A | 7/1912 | Kyria-Kides et al. |
|---|---|---|
| 2,931,787 A | 4/1960 | Jones et al. |
| 2,981,767 A | 4/1961 | Gay et al. |
| 2,984,644 A | 5/1961 | Wheat |
| 3,073,874 A | 1/1963 | Valet et al. |
| 3,253,051 A | 5/1966 | Yanagita et al. |
| 3,258,455 A | 6/1966 | Natta et al. |
| 3,364,190 A | 1/1968 | Emrick |
| 3,568,457 A | 3/1971 | Briggs et al. |
| 3,794,690 A | 2/1974 | Steggerda |
| 3,803,249 A | 4/1974 | Rieve |
| 3,846,338 A | 11/1974 | Kachalova et al. |
| 3,872,216 A | 3/1975 | Kachalova et al. |
| 3,998,755 A | 12/1976 | Hayes |
| 4,049,573 A | 9/1977 | Kaeding |
| 4,163,697 A | 8/1979 | Michaux |
| 4,524,233 A | 6/1985 | Hsu et al. |
| 4,560,822 A | 12/1985 | Holderich et al. |
| 4,704,480 A | 11/1987 | Gefri et al. |
| 5,015,756 A | 5/1991 | Ramachandran et al. |
| 5,210,329 A | 5/1993 | Gomes De et al. |
| 5,393,918 A | 2/1995 | Dobson |
| 5,434,316 A | 7/1995 | Kissinger |
| 5,443,973 A | 8/1995 | Soshiwata et al. |
| 5,567,853 A | 10/1996 | Gupta |
| 5,786,522 A | 7/1998 | Cipullo |

(Continued)

FOREIGN PATENT DOCUMENTS

| EP | 0080449 A1 | 6/1983 |
|---|---|---|
| EP | 0211797 A1 | 2/1987 |

(Continued)

OTHER PUBLICATIONS

Denmark, et al., "Lewis base catalysis in organic synthesis," Angew Chem Int Ed Engl. (2008); 47(9): 1560-1638.

(Continued)

*Primary Examiner* — Sikarl A Witherspoon
(74) *Attorney, Agent, or Firm* — Cooley LLP

(57) ABSTRACT

This present disclosure relates to catalytic processes for upgrading crude and/or refined fusel oil mixtures to higher value renewable chemicals, via mixed metal oxide or zeolite catalysts. Disclosed herein are processes passing a vaporized stream of crude and/or refined fusel oils over various mixed metal oxide catalysts, metal doped zeolites, or non-metal doped zeolites and/or metal oxides providing options to valorize fusel oil mixtures to higher value products. Renewable chemicals formed, via these upgrading catalyst platforms, are comprised of, but not limited to, methyl isobutyl ketone (MIBK), di-isobutyl ketone (DIBK), isoamylene, and isoprene.

71 Claims, No Drawings

(56) References Cited

U.S. PATENT DOCUMENTS

| | | |
|---|---|---|
| 7,067,597 B2 | 6/2006 | Van Egmond et al. |
| 7,090,789 B2 | 8/2006 | Schiodt et al. |
| 7,745,372 B2 | 6/2010 | Li et al. |
| 8,193,402 B2 | 6/2012 | Gruber et al. |
| 8,373,012 B2 | 2/2013 | Peters et al. |
| 8,378,160 B2 | 2/2013 | Gruber et al. |
| 8,450,543 B2 | 5/2013 | Peters et al. |
| 8,487,149 B2 | 7/2013 | Gruber et al. |
| 8,546,627 B2 | 10/2013 | Gruber et al. |
| 9,132,418 B2 | 9/2015 | Shen et al. |
| 10,351,487 B2 | 7/2019 | Smith et al. |
| 2003/0109749 A1 | 6/2003 | Bogan et al. |
| 2004/0192994 A1 | 9/2004 | Bridges et al. |
| 2007/0112220 A1 | 5/2007 | Caers et al. |
| 2010/0150805 A1 | 6/2010 | Serban et al. |
| 2010/0216958 A1 | 8/2010 | Peters et al. |
| 2011/0087000 A1 | 4/2011 | Peters et al. |
| 2012/0171741 A1 | 7/2012 | Peters et al. |
| 2013/0211148 A1 | 8/2013 | Schäfer et al. |
| 2013/0261347 A1 | 10/2013 | Scates et al. |
| 2014/0234929 A1 | 8/2014 | Barr et al. |
| 2015/0217273 A1 | 8/2015 | Sun et al. |
| 2017/0226028 A1 | 8/2017 | Smith et al. |

FOREIGN PATENT DOCUMENTS

| | | |
|---|---|---|
| EP | 0407811 A2 | 1/1991 |
| EP | 0598243 A2 | 5/1994 |
| EP | 1186592 A1 | 3/2002 |
| GB | 673547 A | 6/1952 |
| GB | 1385348 A | 2/1975 |
| GB | 2063297 A | 6/1981 |
| GB | 2093060 A | 8/1982 |
| JP | 2005-253415 A | 9/2005 |
| WO | WO 1997/012654 A1 | 4/1997 |
| WO | WO 2003/053570 A1 | 7/2003 |
| WO | WO 2008/024109 A1 | 2/2008 |
| WO | WO 2010/064652 A1 | 6/2010 |
| WO | WO 2010/099201 A1 | 9/2010 |
| WO | WO 2011/136983 A1 | 11/2011 |
| WO | WO 2014/070354 A1 | 5/2014 |
| WO | WO 2015/005941 A1 | 1/2015 |
| WO | WO 2016/061262 A1 | 4/2016 |

OTHER PUBLICATIONS

Dhaliwal, et al., " Measurement of the Unsaturation of Butyl Rubbers by the Iodine Index Method," Chemistry and Technology (1994); 67(4): 567-581.

Extended European Search Report for European Application No. 15850265.8, dated Apr. 30, 2018, 7 pages.

Garcia, et al., "Simultaneous determination of verapamil and norverapamil in biological samples by high-performance liquid chromatography using ultraviolet detection." J Chromatogr B Biomed Sci Appl. (1997); 693(2): 377-382.

Hutchings, et al., "The Conversion of Methanol and Other O-Compounds to Hydrocarbons over Zeolite β," Journal of Catalysis (1994); 147(1): 177-185.

Jacobsen, et al., "Mesoporous Zeolite Single Crystals," J. Am. Chem. Soc., (2000); 122 (29): 7116-7117.

Klier, et al., "Catalytic synthesis of methanol, higher alcohols and ethers." Catal. Today (1997); 36(1): 3-14.

Küçük and Ceylan, "Potential Utilization of Fusel Oil: A Kinetic Approach for Production of Fusel Oil Esters Through Chemical." Turk J Chem (1998); 22: 289-300.

Liaw, et al., "Determination of morphine by high-performance liquid chromatography with electrochemical detection: application to human and rabbit pharmacokinetic studies." J Chromatogr B Biomed Sci Appl. (1998); 714(2): 237-245.

Liu et al., "A study of ZnxZryOz mixed oxides for direct conversion of ethanol to isobutene," Applied Catalysis A: General (2013); 467: 91-97.

Mitra, et al., "Alkylation of aromatics on zeolite beta. Unusual butylation of benzene with isobutanol." Appl. Catal. A: General (1997); 153(1-2): 233-241.

Mizuno, et al., "One-path and Selective Conversion of Ethanol to Propene on Scandium-modified Indium Oxide Catalysts," Chemical Letters (2012); 41: 892-894.

Montoya, et al., "Colombian fusel oil." Ingenieria e Investigación (2016); 36(2): 21-27.

Murthy et al., "Conversion of ethanol to acetone over promoted iron oxide catalysis," J. Catalysis (1988); 109: 298-302.

Nakajima et al., "Efficient synthesis of acetone from ethanol over ZnO—CaO catalyst," J. Chem Soc. Chem Comm. (1987); 6: 394-395.

PCT/US2015/055581, International Preliminary Report on Patentability dated Apr. 18, 2017, 16 pages.

PCT/US2015/055581, International Search Report and Written Opinion dated Feb. 3, 2016, 19 pages.

PCT/US2019/012395, International Search Report and Written Opinion dated Mar. 8, 2019, 19 pages.

Pereira, et al., "Conversion of Fusel Oil Alcohols to Organic Alkyl Carbonates by Carbon Dioxide Fixation." Conference Presentation, AIChE Annual Meeting, San Francisco, CA, Nov. 8, 2013, 24 pages.

Sikora and Ogonowski, "Coupling of Methanol and Isobutanol to Ethers over γ-Alumina Catalyst. Kinetic Studies." Reaction Kinetics and Catalysis Letters (2000); 70 (Issue 2): 235-241.

Sun, et al., "Direct conversion of bio-ethanol to isobutene on nanosized Zn(x)Zr(y)O(z) mixed oxides with balanced acid-base sites." J Am Chem Soc. (2011); 133(29): 11096-11099.

Tago, et al., "Selective production of isobutylene from acetone over alkali metal ion-exchanged BEA zeolites," Catalysis Today (2011); 164: 158-162.

Tanabe, et al., (Eds.), "New Solid Adds and Bases," Kodansha/Elsevier, Tokyo/Amsterdam, (1989); pp. 260-267.

Vaze, et al., "Electrochemical oxidation of isobutanol to isobutyric acid at nickel oxide electrode: improvement of the anode stability." J. Appl. Electrochem. (1997); 27(5): 584-588.

Irodov, Smirnov and Kryukov, Zh. Org. Khim 18,1401 (1982).

Ivanova and Kucherov, Neftekhimiya vol. 10, 400 (1970).

Nefedova et al., Neftekhimiya vol. 19, 113 (1979).

UPGRADING FUSEL OIL MIXTURES OVER HETEROGENEOUS CATALYSTS TO HIGHER VALUE RENEWABLE CHEMICALS

CROSS-REFERENCE TO RELATED APPLICATIONS

This application claims the priority to and the benefit of U.S. Provisional Application No. 62/613,740, entitled "UPGRADING FUSEL OIL MIXTURES OVER MIXED METAL OXIDE CATALYST TO HIGHER VALUE PRODUCTS" and filed on Jan. 4, 2018; U.S. Provisional Application No. 62/643,103, entitled "UPGRADING FUSEL OIL MIXTURES OVER MIXED METAL OXIDE CATALYST TO HIGHER VALUE PRODUCTS" and filed on Mar. 14, 2018; U.S. Provisional Application No. 62/651,534, entitled "UPGRADING FUSEL OIL MIXTURES OVER MIXED METAL OXIDE CATALYST TO HIGHER VALUE PRODUCTS" and filed on Apr. 2, 2018; U.S. Provisional Application No. 62/695,685, entitled "UPGRADING FUSEL OIL MIXTURES OVER MIXED METAL OXIDE CATALYST TO RENEWABLE PARA-PHENYLENEDIAMINE (PPD) CLASS ANTIOZONANT MIXTURES" and filed on Jul. 9, 2018; U.S. Provisional Application No. 62/696,220, entitled "UPGRADING FUSEL OIL MIXTURES OVER MIXED METAL OXIDE CATALYST TO RENEWABLE MIXTURES OF KETONES HAVING IMPROVED RESIN SOLVATION PROPERTIES" and filed on Jul. 10, 2018; U.S. Provisional Application No. 62/732,749, entitled "UPGRADING FUSEL OIL MIXTURES OVER MIXED METAL OXIDE CATALYST TO RENEWABLE MIXTURES OF KETONES HAVING IMPROVED RESIN SOLVATION PROPERTIES" and filed on Sep. 18, 2018; and U.S. Provisional Application No. 62/755,307, entitled "UPGRADING OF FUSEL OILS OVER MIXED METAL OXIDE CATALYSTS AND ZEOLITES TO ALDEHYDES ISOPRENE AND AROMATICS" and filed on Nov. 2, 2018, the disclosure of each which is hereby incorporated by reference in their entirety.

TECHNICAL FIELD

This disclosure relates to catalytic processes for upgrading crude and/or refined fusel oil mixtures to higher value renewable chemicals via mixed metal oxide or zeolite catalysts.

BACKGROUND

Fusel oils are formed as a by-product of alcoholic fermentation, and consist of a mixture of several alcohols comprised mainly of amyl alcohols along with lesser amounts of propanol, n-butanol, and isobutanol depending upon the purification process employed. In some cases, these fusel oils are re-added back into an ethanol product at some level, burned as fuel, or further purified and sold on the open market. Depending on the carbohydrate source for the fermentation process, and the organism used, fusel oil levels are typically between 0.2-3.0% as a relative percent of the target alcohol produced. Generally, fusel oil alcohols are considered waste compounds in the production of bio-ethanol, and are often burnt as fuel for heating distillation columns.

Some metabolites involved in fermentation processes have been identified as a source of higher alcohols such as fusel oils. Ehrlich (1907) and Klosowski et al. (2010) have attributed the production of higher alcohols to amine nitrogen assimilation. Considering the high content of amyl alcohols in fusel oil (Maiorella et al., 1981), it is important to mention the role played by leucine and isoleucine as source molecules of 3-methyl-1-butanol and 2-methyl-1-butanol, respectively (Ribereau-Gayon et al., 2006). Roehr (2001) indicates that fusel oil is formed from α-keto acids, derived from amino acids. Pfenninger (1963) and Roehr (2001) compared fusel oil composition based on the feedstock for fermentation. Their results indicate that butanol and i-amyl alcohols content increases when molasses and fruits are the raw material for fermentation. However, those authors point out the importance of pH in the fermenter in the production of higher alcohols.

Raw fusel oil is a relatively viscous liquid with a dark-reddish color, and a very unpleasant odor. As a result of these properties, the direct utilization of fusel oil as a solvent has been very limited. In some countries it is burned to supply energy for the ethanol processing plants. In Turkey, it is used mainly for denaturation of alcohol, or for removing the foam from molasses during sugar manufacturing. A substantial portion of it, however, has generally been discarded. Recent studies have suggested that several alternative uses for fusel oils are possible. For example, acetic acid and butyric acid esters, major alcohol components of fusel oil, have economic value as chemicals for flavor and fragrance manufacturing (Ceylan et al, 1997). Especially ethyl butyrate is in high demand as a component of pineapple-banana flavors in the food industry. Seino et. al (1984) investigated the enzymatic synthesis of the carbohydrate esters of fatty acids. Gilles, et. al. (1987) and Welsh and Williams (1989), studied enzymatic esterification of fusel oils with acetic acid and butyric acid. Generally, lipase enzyme was used in these studies. Ghuiba et. al. (1985) investigated chemical esterification of fusel oil with polybasic acids with high molecular weights at relatively high temperatures. They reported the esters synthesized under these conditions are very compatible with polyvinyl chloride as plasticizers. Ay et. al. (1994) reported that fusel oil can be used for the purification of phosphoric acid produced by the wet method. They also reported that especially iso-amyl alcohol and iso-butyl alcohol are selective for extraction of the acid. Hasan et. al. (1993) reported that the indigenously prepared solvent tri-isoamyl phosphate (TAP) obtained from fusel oil has been successfully utilized to extract titanium (IV) from its aqueous solutions. Pereira et al (2013) reported the conversion of main fusel oil components (3-methyl-1-butanol, 2-methyl-1-butanol, and isobutanol) to organic alkyl carbonates by carbon dioxide fixation.

Fusel oil can be also used as a raw material for production of amyl and butyl alcohols which have some different but significant applications: The work of Ogonowski and Sikora (2000) deals with catalytic conversion of methanol and i-butanol into ethers. Similarly, Klier et al. (1997) studied the conversion of higher alcohols into different ethers over multifunctional catalysts. Vaze et al. (1997) presented an alternative of valorization consisting on the electrochemical oxidation of alcohols to produce carboxylic acids. Mitra et al. (1997) studied the alkylation of aromatic compounds with alcohols such as butanol and i-butanol in order to provide green feedstocks to the pharmaceutical industry. Garcia et al. (1997) and Liaw et al. (1998) also offer alternatives for using butanol and i-amyl alcohol in pharmaceutical applications.

Moreover, in the last decade, fusel oils have been used for the manufacture of bio-based products with the advantage of being environmentally safe, renewable, and in some cases biodegradable. Özgülsün et al. (2000) studied the esterification reaction of oleic acid with a fraction of fusel oil from molasses to produce lubricating oil. Dörmo et al. (2004) synthesized a bio-lubricant from fusel oil by enzymatic esterification. Güvenç et al. (2007) and Bandres et al. (2010) performed the syntheses of bio-based solvents to obtain acetates, carbonates and i-valerates with i-amyl alcohol from fusel oil.

SUMMARY OF THE INVENTION

Low cost bio-based fusel oil mixtures can be converted in high yield to crude liquid product mixes consisting of industrially relevant symmetrical and asymmetrical $C_2$-$C_9$ ketones, aldehydes, esters, $C_4$-$C_5$ olefins, and aromatics along with co-production of renewable hydrogen depending upon selected catalysts. Conventional distillation of the crude product mixes provides access to cost competitive industrially relevant renewable chemicals (ie. primarily MIBK, DIBK, isoamylene, isoprene). The distribution and selectivity of the oxygenated or olefinic product mixes can be controlled by adjusting catalyst composition, reaction temperature, and feed composition and flow rates. For example, lower reaction temperatures with a novel mixed metal oxide catalyst results in higher yields to aldehydes relative to ketones, versus higher reaction temperatures giving predominately ketones and lesser amounts of aldehydes. On the other hand, dehydration of fusel oil mixtures provides predominately 3-methyl-1-butene, 1-methyl-2-butene, and 2-methyl-2-butene, which upon in-situ isomerization results in high yields to cost competitive bio-based isoamylene. Alternatively, dehydrogenation of the crude fusel oil alcohol mixture, consisting primarily of 3-methyl-1-butanol and 2-methyl-1-butanol, provides access to the corresponding bio-based $C_5$ aldehydes in excellent yields. Subsequent conversion of the amyl alcohol derived aldehydes (3-methyl butanal and 2-methyl butanal), via novel doped mixed metal oxide catalysts or novel doped zeolite catalysts, provides access to a cost competitive bio-based isoprene in good yields.

In some embodiments, a vaporized stream of crude and/or refined fusel oils is passed over various mixed metal oxide catalysts, metal doped zeolites, or non-metal doped zeolites and/or metal oxides at between 300-500° C. to provide higher value products. In either case, the novel catalysts provide the upgrader with options to valorize fusel oil mixtures to higher value renewable chemicals desired by the chemical industry. Renewable chemicals of interest formed via these upgrading platforms are comprised of but not limited to methyl isobutyl ketone (MIBK), di-isobutyl ketone (DIBK), isoamylene, isoprene, aldehydes, esters, and other asymmetric ketones.

In some embodiments, a process for preparing a renewable chemical includes feeding to a reactor a reactor feed comprising a mixture of $C_3$-$C_6$ alcohols at a concentration of at least about 75 wt. %. The process includes contacting the mixture of $C_3$-$C_6$ alcohols with a mixed oxide catalyst in the reactor, the mixed oxide catalyst having a formula $Zn_v/Mg_w/Cu_x/Mn_y/Zr_z$, whereby the mixture is converted to at least one renewable chemical at a yield of at least about 25 wt. %, wherein V is 1 to 10, wherein W is 1 to 50, wherein X is 0 to 20, wherein Y is 1 to 50, wherein Z is 1 to 180, wherein atomic ratios of each of V and W, relative to Y or Z, are each 1 to 10, and wherein atomic ratios for Y and Z relative to each other is 1 to 16. The atomic ratios for Y and Z relative to each other can be 1 to 6. The atomic ratios for Y and Z relative to each other can also be 2 to 16.

The at least one renewable chemical can be methyl isobutyl ketone (MIBK). The yield of the methyl isobutyl ketone (MIBK) can be at least about 35%, or at least about 45%. The at least one renewable chemical can also be di-isobutyl ketone (DIBK). The yield of the di-isobutyl ketone (DIBK) can be at least about 35%, or at least about 45%. The at least one renewable chemical can also be a $C_5$ aldehyde. The yield of the $C_5$ aldehyde can be at least about 35%, or at least about 45%. The at least one renewable chemical can also be isoprene. The yield of the isoprene can be at least about 35%, or at least about 45%. The at least one renewable chemical can also be isoamylene. The yield of the isoamylene can be at least about 35%, or at least about 45%.

In some embodiments, the process can further include the step of recovering the at least one renewable chemical. The renewable chemical recovered can be methyl isobutyl ketone (MIBK). The renewable chemical recovered can be di-isobutyl ketone (DIBK). The renewable chemical recovered can be a $C_5$ aldehyde. The renewable chemical recovered can be isoprene. The renewable chemical recovered can be isoamylene.

In some embodiments, the mixture of $C_3$-$C_6$ alcohols can be bio-based. At least about 60 wt. %, 70 wt. %, 80 wt. %, 90 wt. %, or 95 wt. % of the mixture of $C_3$-$C_6$ alcohols can be derived from a non-petroleum feedstock. A portion of the mixture of $C_3$-$C_6$ alcohols can produced in an alcohol bio-refinery via fermentation of sugars by yeast. The alcohol bio-refinery can be an ethanol production plant.

In some embodiments, a portion of the mixture of $C_3$-$C_6$ alcohols can be obtained from biomass-generated syngas. A second portion of the mixture of $C_3$-$C_6$ alcohols can be obtained from syngas that has been derived from natural gas, coal, or a combination thereof. The mixture of $C_3$-$C_6$ alcohols can be obtained from a combination of biomass-generated syngas and syngas that has been derived from natural gas, coal, or a combination thereof.

In some embodiments, the reactor feed can include water. The reactor feed can be less than about 15 wt. % water. The reactor feed can be greater than about 10 wt. % water. The reactor feed can be greater than about 5 wt. % water. In some embodiments, the reactor feed can include ethanol. The ethanol can be at a concentration of less than about 20 wt. %. The ethanol can be at a concentration of greater than about 10 wt. %. The ethanol can be at a concentration of greater than about 5 wt. %. The ethanol can be at a concentration of greater than about 2 wt. %.

In some embodiments, the reactor feed can include ethanol, water, and the $C_3$-$C_6$ alcohols. The mixture of $C_3$-$C_6$ alcohols can include at least one of 2-methyl-1-butanol (active amyl alcohol), isoamyl alcohol (isopentanol), isobutyl alcohol, and n-propyl alcohol, propanol, butanol, pentanol, or hexanol. The mixture of $C_3$-$C_6$ alcohols can include two or more of 2-methyl-1-butanol (active amyl alcohol), isoamyl alcohol (isopentanol), isobutyl alcohol, and n-propyl alcohol, propanol, butanol, pentanol, or hexanol.

The mixture of $C_3$-$C_6$ alcohols can be contacted with the mixed oxide catalyst at a temperature within the range of about 300° C. to about 600° C., about 400° C. to about 500° C., about 415° C. to about 470° C., or about 425° C. to about 445° C. The mixture of $C_3$-$C_6$ alcohols can be contacted with the mixed oxide catalyst at a weight hourly space velocity range of about 0.1 hr$^{-1}$ to about 2.5 hr$^{-1}$, about 2.0 hr$^{-1}$, or about 1.5 hr$^{-1}$. The mixed oxide catalyst can be prepared using a hard-template method, a co-precipitation method, or an impregnated method.

In some embodiments, X can be 0 for the mixed oxide catalyst having a formula $Zn_v/Mg_w/Cu_x/Mn_y/Zr_z$. The ratio of $Zn_v/Mg_w/Mn_y/Zr_z$ (V:W:Y:Z) in the mixed oxide catalyst can be about 1:2:5:18. The ratio of $Zn_v/Mg_w/Mn_y/Zr_z$ (V:W:Y:Z) in the mixed oxide catalyst can be about 1:4:5:18. The ratio of $Zn_v/Mg_w/Mn_y/Zr_z$ (V:W:Y:Z) in the mixed oxide catalyst can be about 2:1:5:18. The ratio of $Zn_v/Mg_w/Mn_y/Zr_z$ (V:W:Y:Z) in the mixed oxide catalyst can be about 2:2:5:18.

In some embodiments, a process is disclosed for preparing a renewable chemical including feeding to a reactor a reactor feed comprising a mixture of $C_3$-$C_6$ alcohols at a concentration of at least about 75 wt. %, and contacting the mixture of $C_3$-$C_6$ alcohols with a mixed oxide catalyst in the reactor, the mixed oxide catalyst having a formula $Zn_v/Mg_w/Cu_x/Mn_y/Zr_z$, whereby the mixture is converted to at least one renewable chemical at a yield of at least about 25 wt. %, wherein V is 0 to 10, wherein W is 0 to 50, wherein X is 0 to 20, wherein Y is 1 to 50, wherein Z is 1 to 180, wherein atomic ratios of each of V and W, relative to Y or Z, are each 0 to 10, and wherein atomic ratios for Y and Z relative to each other is 3 to 6.

The at least one renewable chemical can be methyl isobutyl ketone (MIBK). The yield of the methyl isobutyl ketone (MIBK) can be at least about 35%, or at least about 45%. The at least one renewable chemical can also be a di-isobutyl ketone (DIBK). The yield of the di-isobutyl ketone (DIBK) can be at least about 35%, or at least about 45%. The at least one renewable chemical can also be a $C_5$ aldehyde. The yield of the $C_5$ aldehyde can be at least about 35%, or at least about 45%. The at least one renewable chemical can also be isoprene. The yield of the isoprene can be at least about 35%, or at least about 45%. The at least one renewable chemical can also be isoamylene. The yield of the isoamylene can be at least about 35%, or at least about 45%.

In some embodiments, the process can further include the step of recovering the at least one renewable chemical. The renewable chemical recovered can be methyl isobutyl ketone (MIBK). The renewable chemical recovered can be di-isobutyl ketone (DIBK). The renewable chemical recovered can be a $C_5$ aldehyde. The renewable chemical recovered can be isoprene. The renewable chemical recovered can be isoamylene.

In some embodiments, the mixture of $C_3$-$C_6$ alcohols can be bio-based. At least about 60 wt. %, 70 wt. %, 80 wt. %, 90 wt. %, or 95 wt. % of the mixture of $C_3$-$C_6$ alcohols can be derived from a non-petroleum feedstock. A portion of the mixture of $C_3$-$C_6$ alcohols can produced in an alcohol bio-refinery via fermentation of sugars by yeast. The alcohol bio-refinery can be an ethanol production plant.

In some embodiments, a portion of the mixture of $C_3$-$C_6$ alcohols can be obtained from biomass-generated syngas. A second portion of the mixture of $C_3$-$C_6$ alcohols can be obtained from syngas that has been derived from natural gas, coal, or a combination thereof. The mixture of $C_3$-$C_6$ alcohols can be obtained from a combination of biomass-generated syngas and syngas that has been derived from natural gas, coal, or a combination thereof.

In some embodiments, the reactor feed can include water. The reactor feed can be less than about 15 wt. % water. The reactor feed can be greater than about 10 wt. % water. The reactor feed can be greater than about 5 wt. % water. In some embodiments, the reactor feed can include ethanol. The ethanol can be at a concentration of less than about 20 wt. %. The ethanol can be at a concentration of greater than about 10 wt. %. The ethanol can be at a concentration of greater than about 5 wt. %. The ethanol can be at a concentration of greater than about 2 wt. %.

In some embodiments, the reactor feed can include ethanol, water, and the $C_3$-$C_6$ alcohols. The mixture of $C_3$-$C_6$ alcohols can include at least one of 2-methyl-1-butanol (active amyl alcohol), isoamyl alcohol (isopentanol), isobutyl alcohol, and n-propyl alcohol, propanol, butanol, pentanol, or hexanol. The mixture of $C_3$-$C_6$ alcohols can include two or more of 2-methyl-1-butanol (active amyl alcohol), isoamyl alcohol (isopentanol), isobutyl alcohol, and n-propyl alcohol, propanol, butanol, pentanol, or hexanol.

The mixture of $C_3$-$C_6$ alcohols can be contacted with the mixed oxide catalyst at a temperature within the range of about 300° C. to about 600° C., about 400° C. to about 500° C., about 415° C. to about 470° C., or about 425° C. to about 445° C. The mixture of $C_3$-$C_6$ alcohols can be contacted with the mixed oxide catalyst at a weight hourly space velocity range of about 0.1 $hr^{-1}$ to about 2.5 $hr^{-1}$, about 2.0 $hr^{-1}$, or about 1.5 $hr^{-1}$. The mixed oxide catalyst can be prepared using a hard-template method, a co-precipitation method, or an impregnated method. In some embodiments, the ratio of $Zn_v/Mg_w/Mn_y/Zr_z$ (V:W:Y:Z) in the mixed oxide catalyst is about 0:0:5:18, about 0:2:5:18, about 1:0:5:18, or about 2:0:5:18.

In some embodiments, a process is disclosed for converting one or more $C_2$-$C_6$ linear or branched alcohols contained in fusel oil to renewable chemicals, including contacting a feed stream with the $C_2$-$C_6$ linear or branched alcohols with a catalyst to produce at least one of a ketone, an olefin, a di-olefin, or an aldehyde. The one or more $C_2$-$C_6$ linear or branched alcohols can include at least 50 wt. % of organic material within the fusel oil. The catalyst can include mixed metal oxide manganese/zirconium catalysts, doped with magnesium, zinc, copper, or combinations thereof.

In some embodiments, the catalyst can include mixed acidic ZSM-5 zeolite catalysts, doped with boron, phosphorous, or combinations thereof. In some embodiments, the catalyst can include mixed niobium/alumina catalysts, doped with boron, phosphorous, or combinations thereof. In some embodiments, the catalyst can include a zinc oxide catalyst. In some embodiments, the catalyst can include mixed Y-alumina catalysts, doped with potassium, or combinations thereof.

In some embodiments, the manganese/zirconium support can further include from about 0.01 wt. % to about 20 wt. % manganese and 35-70% zirconium. In some embodiments, the manganese/zirconium support can further include from about 0.01 wt. % to about 10 wt. % magnesium and 0.01 wt. % to about 10 wt. % zinc, and 0.01 wt. % to about 10 wt. % copper, or combinations thereof.

In some embodiments, the mixed acidic ZSM-5 catalyst can further include from about 0.01 wt. % to about 20 wt. % boron, and 0.01 wt. % to about 20 wt. % phosphorous. In some embodiments, the niobium/alumina support can further include from about 0.01 wt. % to about 20 wt. % niobium and 35-70 wt. % alumina. In some embodiments, the niobium/alumina support can further include from about 0.01 wt. % to about 20 wt. % boron, and 0.01 wt. % to about 20 wt. % phosphorous. In some embodiments, the Y-alumina catalyst can further include from about 0.01 wt. % to about 20 wt. % potassium.

DETAILED DESCRIPTION

The ability to transform low cost bio-based fusel oils into highly desired bio-based oxygenates has not previously been reported or demonstrated. Disclosed herein are catalysts and processes that are suitable for converting fusel oils heavier oxygenates.

Oxygenated solvents such as aliphatic ketones constitute the largest segment of the solvent market. For example, diisobutyl ketone (DIBK), methyl isoamyl ketone (MIAK) and their alcohol products carbinols have a market volume of around 80 million pounds per year. With an annual production of 1 billion pounds, methyl isobutyl ketone (MIBK) is among the top ten most widely used organic solvents in industry. At present, the manufacturing processes of ketones are relatively complicated. For example, the petroleum-derived raw material acetone is chemically processed to MIBK via three reaction steps: (i) aldol condensation to diacetone alcohol, (ii) dehydration to mesityl oxide and (iii) selective hydrogenation of the unsaturated ketone mesityl oxide. Similarly, following the three-step process, the carbonyl compound isobutanal or MIBK reacts with acetone to yield MIAK or DIBK. Although multifunctional catalysts have been developed to enable these reaction series in one pot, the yield to MIBK or DIBK is only around 30% or 10%, respectively. In addition, the operation requires high pressure (10-100 atm), and the supply of raw materials is dependent on the availability of petroleum feedstock Isoprene is the requisite building block for polyisoprene rubber, styrene co-polymers, and butyl rubber. Currently all commercially available isoprene is derived from petroleum. The majority of isoprene has typically been produced by separating the $C_5$ stream from ethylene crackers fed with heavier feedstocks like naphtha or gas oil. Recently, steam crackers in the United States have shifted toward using lighter feedstocks like ethane, propane, and butane, which are byproducts of shale gas production. These lighter feedstocks have increased ethylene yields but have negatively impacted isoprene production. This has created a favorable opportunity for bio-based isoprene to enter the market. Bio-based isoprene, produced by aerobic bioconversion of carbohydrates, is identical to petroleum-based isoprene and functions as a drop-in replacement molecule. Production of isoprene from biological sources is in the early stages of development but is accelerating with the backing from major tire manufacturers (Bridgestone, Goodyear, and Michelin). Total world consumption of isoprene in 2008 was 800,000 metric tons (GlycosBio 2010). About 60% of it was used to produce polyisoprene rubber, styrene co-polymers, and butyl rubber used for manufacturing tires. About 30% was used to produce adhesives and the balance was used for medical or personal care applications. Tires are the dominant market for isoprene and demand for isoprene-based products typically follows the health of the transportation sector. In 2013, Russia and the United States account for roughly two-thirds of the total world consumption of isoprene (IHS 2014e).

In former times, a potentially economical process for production of isoprene is the dehydration of 2-methylbutyraldehyde (2-MBA). 2-MBA can be produced by hydroformylation of butene, and so is an inexpensive raw material which can be manufactured in the large quantities needed for large scale commercial production of isoprene. The dehydration of 2-MBA to isoprene is catalyzed by acids and can be affected with reasonable selectivity. However, since isoprene itself is polymerized by strong acids such as sulfuric acid, such strong acids are not useful as isoprene catalysts. A wide variety of catalysts, including both molecular sieves and various other materials, have been proposed for use in the previous reactions for production of isoprene and in chemically-similar reactions. For example, British Pat. No. 673,547 describes a process for the conversion of 1-methoxy-3-methylbut-4-ene to isoprene using a silicate of aluminum as the catalyst. U.S. Pat. No. 3,253,051 to Yanagita et al. describes a process for the production of isoprene from a mixture of isobutylene and formaldehyde in which the catalyst employed is a mixture of an oxide or hydroxide of a metal such as iron with phosphoric acid, this mixture being supported on a suitable carrier, for example silica or alumina. U.S. Pat. Nos. 3,872,216 and 3,846,338, both to Kachalova et al., describe methods for producing isoprene from a dioxane employing a tricalcium phosphate catalyst. British Pat. No. 1,385,348 describes the production of a diene from the corresponding aldehyde using an acidic dehydration catalyst, which can comprise inorganic acids, inorganic acid salts, acid anhydrides of an inorganic acid, or mixed anhydrides thereof either supported or unsupported. Specific catalysts mentioned include phosphoric acid, boric acid, silicic acid, titanic acid, boron phosphate, silicon borate, and silicon titanate. British Pat. No. 2,093,060 describes the dehydration of carbonyl compounds to dienes using as catalysts magnesium phosphate compositions, while British Pat. No. 2,063,297 describes the use of alum and mixed alum sulfates as catalysts in the same reaction. Zeolite molecular sieves have been used as catalysts for production of isoprene by dehydration of starting materials other than 2-MBA. For example, Japanese Patent Application Publication No. 77/57104 describes the dehydration of 4,4-DMD in the gas phase over Group II metal-exchanged Zeolite X. Japanese Patent Application Publication No. 74/10924 describes the dehydration of 4,4-DMD or 4-methyl-5,6-dihydro-2H-pyran in the gas phase over a zeolite catalyst. Japan Patent Application Publication No. 77/36603 describes the dehydration of 4,4-DMD over a catalyst composed of Zeolite X and an acid clay. Nefedova et al., Neftekhimiya 19, 113 (1979) describe the dehydration of 2-methylbutane-2,3-diol using as catalysts Zeolites A, X, and Y. Ivanova and Kucherov, Neftekhimiya 10, 400 (1970) describe the use of Zeolite Y as a catalyst for the dehydration of dimethylvinyl-carbinol. A variety of catalysts have also been proposed for use in the dehydration of 2-methylbutyraldehyde to isoprene. U.S. Pat. No. 1,033,180 describes the use of aluminum silicate as a catalyst. European Patent Application Publication No. 80,449 describes the use of acidic, heterogeneous catalysts, specifically boron phosphate and silica in this reaction. U.S. Pat. No. 4,524,233 describes the use of boron phosphate admixed with graphite and treated with amines and steam as a 2-MBA to isoprene catalyst. U.S. Pat. No. 721,116 and Bol'shakov et al., Neftekhimiya 23, 183 (1983) describe the use of boron phosphate as a catalyst for this reaction. Irodov, Smirnov and Kryukov, Zh. Org. Khim. 18,1401 (1982) describe the use of amorphous aluminum, boron and calcium phosphates as catalysts for the conversion of 2-MBA to isoprene. U.S. Pat. No. 4,560,822 to Hoelderich et al. (which issued Dec. 24, 1985 on Application Ser. No. 730,687 filed May 3, 1985 and claiming priority of West German Patent Application No. 34 19379 filed May 24, 1984) describes and claims a process for the dehydration of aldehydes to dienes (including the dehydration of 2-methylbutyraldehyde to isoprene) at elevated temperatures using a zeolite as a catalyst. European Patent Application Publication No. 0211797A1 (1985, Goodyear) describes the use of a boron phosphate catalyst treated with ammonium carbonate or ammonium bicarbonate followed by calcination presumably to produce a large pore catalyst for dehydration of 2-MBA to isoprene resulting in longer on-stream times (120 hr versus 6 hr) with slower decay in activity. However, no mention is made regarding extended catalyst life and selectivity as a result of multiple regenerations.

A disadvantage associated with the aforementioned boron-phosphate catalysts to dehydrate aldehydes is that catalyst life depends on many factors which include catalyst composition and structure, catalyst activity, operating temperatures, surface phosphor leaching, and coke deposition. Coke deposition is understood to denote coke (carbonaceous) deposits formed on the catalyst during the dehydration reaction. As stated earlier, no commercial process based on said technique has been developed so far, since there is no catalyst with selectivity and stability to justify a commercial process, and the cost to produce 2-MBA as a feedstock to isoprene is not cost competitive compared to the extraction of isoprene from crude $C_5$ refinery streams.

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

In this application, the use of "or" means "and/or" unless stated otherwise.

As used throughout the specification, "a" can include referents to the singular or plural. For example, an alcohol can include one or more than one alcohol.

Throughout the present specification, the terms "about" and/or "approximately" can be used in conjunction with numerical values and/or ranges. The term "about" is understood to mean those values near to a recited value. For example, "about 40 [units]" can mean within ±25% of 40 (e.g., from 30 to 50), within ±20%, ±15%, ±10%, ±9%, ±8%, ±7%, ±6%, ±5%, ±4%, ±3%, ±2%, ±1%, less than ±1%, or any other value or range of values therein or there below. Furthermore, the phrases "less than about [a value]" or "greater than about [a value]" should be understood in view of the definition of the term "about" provided herein. The terms "about" and "approximately" can be used interchangeably.

Throughout the present specification, the term "renewable chemical" is used to indicate the product or products of a process described herein. In broad terms, a renewable chemical is a bio-based material intentionally made from substances derived from living (or once-living) organisms. Renewable chemicals include linear, branched, and cyclic molecules having up to about 12 carbons. The terms include either a homologated (one carbon added relative to the carbon number of the starting material) or lengthened (two or more carbons added relative to the carbon number of the starting material) compounds, or a product with the same or greater carbon number relative to the starting material but with some sort of functionalization introduced (e.g., a carbonyl, a hydroxyl, ester, and/or a degree of unsaturation, e.g., a double bond), and mixtures thereof. Non-limiting examples of co-products including renewable chemicals produced by a process disclosed herein include methyl isobutyl ketone (MIBK), sec-butyl methyl ketone (iso-MIBK), di-isobutyl ketone (DIBK), 2,5-dimethyl-4-heptanone (iso-DIBK), isoamylene, isoprene, aldehydes, esters, and other asymmetric ketones.

Co-products may also be produced by a catalytic reaction, according to the catalysts and processes of the present application. For example, co-products include a product obtained from the reaction of at least one reactant with at least one intermediate, or a product obtained from the reaction of multiple intermediates. Co-products include linear, branched, cyclic molecules having up to about 10 carbons. Co-products also includes non-hydrocarbon molecules generated by a process of converting starting material. Non-limiting examples of co-products produced by a process disclosed herein include, isobutylene, acetone, hydrogen, carbon dioxide, methane, phenol, 2-pentanone, mesityl oxide, methyl isobutylketone, 3-methyl-2-butanone, 2-methyl phenol, 3-methyl phenol (meta-cresol), 2,5-dimethyl phenol, 3,5-dimethyl phenol (3,5-xylenol), 2,3-dimethyl phenol, and 3,4-dimethyl phenol.

Throughout the present specification, the term "selectivity" is used to indicate the selectivity of the process to produce a particular renewable chemical. In some embodiments, the catalyst, preparation of the catalyst, and reaction parameters, e.g., superficial velocity, influence the yield of a particular renewable chemical.

"Natural" products are defined as materials derived from natural materials (ie. plant based materials, fermentation broth, etc.) added to flavor and fragrance compounds which have not been subjected to a chemical transformation other than a simple distillation step.

As used herein, the term "yield" in reference to a yield of a renewable chemical, e.g., MIBK, is expressed as a percentage of the maximum theoretical yield, which defines the maximum amount of the renewable chemical, e.g., isoprene, that can be generated per a given amount of fusel oils as dictated by the stoichiometry of the catalytic reaction used to make the renewable chemical, e.g., isoprene. For example, the theoretical yield for the catalytic reaction described herein is 33.3%, i.e., 1 mol of MIBK produced per every 3 mols of substrate in the reactor feed. As such, if 24% of the carbon substrate is converted to MIBK, the yield, as used herein, would be expressed as 72%, which is obtained by taking a 24% conversion to MIBK divided by a potential 33.3% maximum theoretical yield. In another example, the theoretical yield for the catalytic reaction described herein is 50%, i.e., 1 mol of DIBK produced per every 2 mols of carbon substrate in the reactor feed. As such, if 40% of the carbon substrate is converted to DIBK, the yield, as used herein, would be expressed as 80.0%, which is obtained by taking a 40% conversion to DIBK divided by a potential 50% maximum theoretical yield. Conversely, on a carbon atom basis, the theoretical yield to DIBK is 75%, which is expressed as 3 carbon atoms in DIBK (1 mol) divided by 4 carbon atoms from the reactor feed substrate (2 mols).

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The word "about" when immediately preceding a numerical value means a range of plus or minus 10% of that value, e.g., "about 50" means 45 to 55, "about 25,000" means 22,500 to 27,500, etc. Furthermore, the phrases "less than about" a value or "greater than about" a value should be understood in view of the definition of the term "about" provided herein.

"Fusel oil", also known as fusel oil alcohols or fusel alcohols, is typically a mixture of one or more alcohols ($C_3$-$C_6$) such as 2-methyl-1-butanol (active amyl alcohol), isoamyl alcohol (isopentanol), isobutyl alcohol, and n-propyl alcohol, propanol, butanol, pentanol, and hexanol, but not methanol and ethanol. "Crude" fusel oil mixtures are defined by higher levels of $C_2$-$C_4$ alcohols and water as a result of less rigorous downstream separation of typical $C_5$ fusel alcohols (3-methyl-1-butanol and 2-methyl-1-butanol) from ethanol. Whereas, "refined" fusel oil mixtures are defined by a higher concentration of $C_5$ alcohols (e.g. amyl alcohols), relative to $C_2$-$C_4$ alcohols, and normally lesser amounts of water.

In some embodiments, ketone product mixtures can be produced with high selectivity and high yields, via a single catalytic step, from fusel oil upgrading, to provide methyl isobutyl ketone (MIBK), sec-butyl methyl ketone (iso-MIBK), di-isobutyl ketone (DIBK), and 2,5-dimethyl-4-heptanone (iso-DIBK) derived from 3-methyl 1-butanol and 2-methyl 1-butanol. Higher selectivities and yield to MIBK, relative to DIBK formation, can be achieved by co-feeding additional amounts of ethanol relative to the crude fusel oils.

In the first approach, fusel oil mixtures can be converted to a crude liquid product mix consisting of $C_3$-$C_9$ ketones, aldehydes, hydrogen, and lesser amounts of $C_2$-$C_5$ olefins. The distribution of the oxygenated product mix can be controlled by reaction temperature and feed flow rates. For example, lower reaction temperatures result in higher yields to aldehydes, and higher reaction temperatures result in predominately ketones. Depending on the type of metal oxides, and their relative metal ratios, fusel oil mixtures can be converted to a liquid product in >90% mass accountability consisting primarily of $C_5$ aldehydes along with lesser amounts of methyl isobutyl ketone, di-isobutyl ketone, and $C_3$-$C_7$ ketones with up to 2.3 eq of hydrogen relative to the average molecular weight of the fusel oil mixture.

At higher reaction temperatures, fusel oil mixtures can be converted to a liquid product with >60% mass accountability consisting primarily of methyl isobutyl ketone (MIBK), di-isobutyl ketone (DIBK), $C_5$ aldehydes, and lesser amounts of $C_3$-$C_7$ ketones with up to 3.0 eq of hydrogen relative to the average molecular weight of the fusel oil mixture. Theoretically, the highest liquid mass accountability, assuming 100% yield from alcohol to ketone, is 80% due to $CO_2$ and hydrogen formation, via a series of reactions over the mixed metal oxide catalyst. One skilled in the art will recognize the versatility of converting mixtures of alcohols ($C_2$-$C_5$) to value added aldehydes, or symmetrical and asymmetrical ketones difficult to prepare.

One skilled in the art will recognize the benefits of converting mixtures of bio-based alcohols including fusel oils into value added aldehydes, or symmetrical and asymmetrical target ketones that are normally difficult to prepare. For example, the addition of renewable based ethanol to the fusel oil feed results in increased levels of MIBK with a corresponding decrease in DIBK formation, and increased levels of renewable 6-methyl-2-heptanone (CAS #928-68-7) and 6-methyl-3-heptene-2-one (CAS #20859-10-3), which both find use as key raw materials towards synthesis of Vitamin E. Additionally, m-cresol (CAS#108-39-4) levels are increased, which finds use in the total synthesis of Thymol and other applications. Examples of reactor effluent compositional data for crude fusel oil with additional ethanol mixtures is exemplified in Tables 21-24. Alternatively, adding bio-based or petroleum-based methanol to the feed, or operating with only methanol as the feed, results in formation of additional amounts of hydrogen or primarily hydrogen. This allows for the adjustment of the level of hydrogen produced depending upon the needs of production and the product portfolio.

In a second approach, fusel oil mixtures can be directly converted, over a metal doped zeolite, to a crude liquid mixture with >60% mass accountability consisting primarily of typical BTX aromatics (i.e. toluene, m-xylene, p-xylene, o-xylene, ethyl benzene, trimethylbenzenes, etc) with p-xylene as the predominant xylenes isomer along with minor amounts of $C_3$-$C_7$ olefins. The remaining unaccounted for mass are $C_2$-$C_4$ olefins, as measured in the uncondensed vapor stream. From a practical standpoint, the aromatic compounds can be separated, via classical unit operations, for marketing as renewable chemicals, and the resulting $C_2$-$C_7$ olefins can either be recycled to increase yields to aromatic compounds, or oligomerized to a renewable based fuel.

In the third approach, fusel oil mixtures are quantitatively dehydrated to their corresponding $C_2$-$C_5$ olefins. Depending on the catalyst used for dehydration (γ-Alumina), the primary $C_5$ olefins can be converted to 3-methyl-1-butene (70%) and 2-methyl-1-butene (10%) with minor amounts of isomerization to the 2-methyl-2-butene isomer (18%), or the use of base treated γ-Alumina catalyst can further reduce the level of isomerization resulting in higher purities of 3-methyl-1-butene (U.S. Pat. No. 4,234,752). These terminal olefins, along with the lesser amounts of $C_2$-$C_4$ olefins, can be oligomerized to Jet or Diesel fuel, with varying fuel properties, depending upon catalyst and reaction conditions.

Conversely, in-situ isomerization of primary $C_5$ alcohols is accomplished, via metal doped zeolites (Zn-ZSM5, ZnZr-H-FER), or γ-Alumina at higher reaction temperatures, resulting in an olefinic mixture consisting of 2-methyl-2-butene isomer (62%), 2-methyl-1-butene (22%), 2-pentene (12%), and minor amounts of 3-methyl-1-butene (4%). The isomerized $C_5$ olefins, along with the lesser amounts of $C_2$-$C_4$ olefins, can be oligomerized to Jet or Diesel fuel, with varying fuel properties, depending upon catalyst and reaction conditions, or used as monomers. These low carbon intensity $C_2$-$C_5$ olefin streams can be directly oligomerized 'as-is' to produce a low carbon fuel (e.g. Gasoline, Jet, or diesel), or may be co-mingled with other olefin streams derived from renewable, or non-renewable, based alcohols in order to reduce the overall carbon footprint of the target fuel.

Changes in metal oxide ratios, and/or metal oxide combinations, results in an ability to alter product selectivity depending on the crude fusel oil composition, processing parameters, and the target products desired. For example, preferred metal oxide combinations, and their relative metal atomic molar ratios (see parenthetical values) provides the oxygenated product distributions shown in the examples below depending upon reaction parameters: $Zn_v/Mg_w/Mn_y/Zr_z$ (1/2/5/18), $Zn_v/Mg/Zr_z$ (1/2/24), $Zn_v/Zr_z$ (1/11), $Mn_y/Zr_z$ (5/18), $Zn_v/Cu_x/Mg_w/Zr_z$ (1/1/5/18), $Zn_v/Mn_y/Zr_z$ (1/5/18), $Mg_w/Mn_y/Zr_z$ (2/5/18), $Mg_w/Zr_z$ (1/12), $Cu_x/Zr_z$ (2/12), ZnO. The preferred ranges of atomic metal ratios for $Zn_v$, $Mg_w$, and $Cu_x$, relative to $Mn_y$ or $Zr_z$, are typically 1 to 10. The preferred ranges of atomic metal ratios for $Mn_y$ and $Zr_z$ relative to one another is 1 to 6 and 2 to 16, respectively. In some embodiments, a process for preparing a renewable chemical includes feeding to a reactor a reactor feed comprising a mixture of $C_3$-$C_6$ alcohols at a concentration of at least about 75 wt. %. The process includes contacting the mixture of $C_3$-$C_6$ alcohols with a mixed oxide catalyst in the reactor, the mixed oxide catalyst having a formula $Zn_v/Mg_w/Cu_x/Mn_y/Zr_z$, whereby the mixture is converted to at least one renewable chemical at a yield of at least about 25 wt. %, wherein V is 1 to 10, wherein W is 1 to 50, wherein X is 0 to 20, wherein Y is 1 to 50, wherein Z is 1 to 180, wherein atomic ratios of each of V and W, relative to Y or Z, are each 1 to 10, and wherein atomic ratios for Y and Z relative to each other is 1 to 16. The atomic ratios for Y and Z relative to each other can be 1 to 6. The atomic ratios for Y and Z relative to each other can also be 2 to 16. In some embodiments, X can be 0 for the mixed oxide catalyst having a formula $Zn_v/Mg_w/Cu_x/Mn_y/Zr_z$. The ratio of $Zn_v/Mg_w/Mn_y/Zr_z$ (V:W:Y:Z) in the mixed oxide catalyst can be about 1:2:5:18. The ratio of $Zn_v/Mg_w/Mn_y/Zr_z$ (V:W:Y:Z) in the mixed oxide catalyst can be about 1:4:5:18. The ratio of $Zn_v/Mg_w/Mn_y/Zr_z$ (V:W:Y:Z) in the mixed oxide catalyst can be about 2:1:5:18. The ratio of $Zn_v/Mg_w/Mn_y/Zr_z$ (V:W:Y:Z) in the mixed oxide catalyst can be about 2:2:5:18.

In some embodiments, a process is disclosed for preparing a renewable chemical including feeding to a reactor a reactor feed comprising a mixture of $C_3$-$C_6$ alcohols at a concentration of at least about 75 wt. %, and contacting the mixture of $C_3$-$C_6$ alcohols with a mixed oxide catalyst in the reactor, the mixed oxide catalyst having a formula $Zn_v/Mg_w/Cu_x/Mn_y/Zr_z$, whereby the mixture is converted to at least one renewable chemical at a yield of at least about 25 wt. %, wherein V is 0 to 10, wherein W is 0 to 50, wherein X is 0 to 20, wherein Y is 1 to 50, wherein Z is 1 to 180, wherein atomic ratios of each of V and W, relative to Y or Z, are each 0 to 10, and wherein atomic ratios for Y and Z relative to each other is 3 to 6. In some embodiments, the ratio of $Zn_v/Mg_w/Mn_y/Zr_z$ (V:W:Y:Z) in the mixed oxide catalyst is about 0:0:5:18, about 0:2:5:18, about 1:0:5:18, or about 2:0:5:18.

The catalysts may be prepared via classical techniques (ie. incipient wetness impregnation, co-precipitation, hard-template method, a co-precipitation method, an impregnated method, etc.), but impregnation is preferred with regard to cost and ease of preparation. Metal oxide catalysts may be regenerated in-situ, via air, as necessary to return catalyst to its initial activity. To maintain product distributions with high selectivity to oxygenated products, the zirconium oxide support must be sufficiently moderated to prevent significant amounts of $C_2$-$C_5$ alcohol dehydration to the $C_5$ olefins. This is most effectively done by addition of metals Zn, Mn, Mg, Cu, and combinations thereof. Other metals and non-metals capable of moderating the acidity of the zirconium or aluminum oxide support with are: Ca, Sc, Ti, V, Nb, Cr, Fe, Co, Ni, Ga, Mo, Ru, Rb, Sr, Cs, Ba, In, Cd, Sn, Al, Si, Bi, W, Re, P, B. The examples provided show an overview of the fusel oil upgrading technology relative to catalyst compositions as discussed above (see Tables 1-20). Unless noted otherwise, catalysts were prepared via the incipient wetness impregnation technique.

One issue with fusel oil upgrading technology to primarily aldehydes, via acceptorless dehydrogenation, is the inability to separate 3-methyl-butanal and 2-methyl-butanal via conventional distillation. This prevents the isolation and harvesting of the full market value associated with renewable 3-methyl-butanal (isovaleraldehyde) and/or 2-methyl-butanal, which are useful as a raw materials throughout the flavor, fragrance and fine chemicals industries. In one aspect, the application relates to a process of indirect separation of the aldehyde mixture by utilizing mixed metal oxide catalysts, with and without phosphorous and/or boron or metal and non-metal doped Zeolites, which convert the aldehyde mixture to isoprene and methyl substituted pentenes (e.g. 3-methyl-1-butene, 2-methyl-1-butene, and 2-methyl-2-butene). Subsequent purification of the isoprene rich mixture, via extractive distillation, provides access to bio-based monomer grade isoprene, isoamylene, and/or 3-methyl-1-butene. This approach results in purification of the 3-methyl-butanal and 2-methyl-butanal aldehyde product mixture (~75/25 ratio) to >85% 3-methyl-butanal purity with co-production of renewable isoprene, isoamylene, and lesser amounts of isobutylene. Conversely, if isoprene and isoamylene are the desired end products, recycling of the aldehyde mixture provides high yields to isoprene and isoamylene after purification via conventional extractive distillation.

In some embodiments, the at least one renewable chemical can be methyl isobutyl ketone (MIBK). The yield of the methyl isobutyl ketone (MIBK) can be at least about 35%, or at least about 45%. The at least one renewable chemical can also be di-isobutyl ketone (DIBK). The yield of the di-isobutyl ketone (DIBK) can be at least about 35%, or at least about 45%. The at least one renewable chemical can also be a $C_5$ aldehyde. The yield of the $C_5$ aldehyde can be at least about 35%, or at least about 45%. The at least one renewable chemical can also be isoprene. The yield of the isoprene can be at least about 35%, or at least about 45%. The at least one renewable chemical can also be isoamylene. The yield of the isoamylene can be at least about 35%, or at least about 45%.

In some embodiments, the process can further include the step of recovering the at least one renewable chemical. The renewable chemical recovered can be methyl isobutyl ketone (MIBK). The renewable chemical recovered can be di-isobutyl ketone (DIBK). The renewable chemical recovered can be a $C_5$ aldehyde. The renewable chemical recovered can be isoprene. The renewable chemical recovered can be isoamylene.

In another aspect, the application relates to a fusel oil upgrading process providing the ability to remove natural products from fusel oils in an economical manner, while still maintaining a natural product classification. For example, vaporization of the crude fusel oil mixture at 140-180° C., as part of the fusel oil upgrading process, results in the ability to remove a crude heavy organic stream prior to entering the fixed reactor bed. The heavy organic stream which typically represents 1-2 wt. % of the total fusel oil weight contains several attractive natural products such as: 2-phenyl ethanol, ethyl caprylate, 2-phenyl ethyl acetate, ethyl caprate, ethyl laurate, and ethyl palmitate at varying levels depending upon fermentation conditions and feedstock. Previously, it was be uneconomical to distill and condense 98-99% of the crude fusel oil mixture overhead only to recover a small natural product fraction. However, according to the present fusel oil upgrading process, the removal of the natural product stream coupled with upgrading the entire vaporized fusel oil stream to higher value products provide the practitioner with an economical approach to harvest the value from the natural products contained within.

Changes in metal oxide ratios, non-metal and/or metal oxide combinations, and/or metal and non-metal doped zeolites provides the ability to alter product selectivity to isoprene. For example, preferred metal oxide combinations, and zeolite catalyst combinations and their relative metal weight percent ratios (see parenthetical values) provides crude isoprene distributions shown in the Tables below (see Tables 25-31) depending upon reaction parameters: NbO, Nb/Alu, Nb/Alu/B, Nb/Alu/B/P, zeolite/boron, and zeolite/B/P. The catalysts may be prepared via classical techniques (ie. incipient wetness impregnation, co-precipitation, hard-template method, a co-precipitation method, an impregnated method, etc.), but impregnation is preferred with regard to cost and ease of preparation. Metal oxide and zeolite catalysts may be regenerated in-situ, via air, as necessary to return catalyst to its' initial activity. Unless noted otherwise, catalysts were prepared via the incipient wetness impregnation technique.

Catalysts and processes according to the present disclosure in which mixed metal oxide catalysts, non-metal doped mixed metal oxide catalysts, zeolites, and metal or non-metal doped zeolite are used in fusel oil upgrading reactions provide flexibility to produce industrially relevant renewable chemicals such as ketones, olefins, di-olefins, and/or aldehydes in high yield and selectivity at competitive costs.

Granular or extruded catalysts are suitable for the reactions even though no specific size and morphology are required. Catalyst with a size greater than 0.1 mm is preferred, and the size of 0.2-1.0 mm is more preferred for the operation ability and low pressure drop.

In some embodiments, the reactor feed can include water. The reactor feed can be vaporized prior to entering the reactor. The reactor feed can be less than about 15 wt. % water. The reactor feed can be greater than about 10 wt. % water. The reactor feed can be greater than about 5 wt. % water. In some embodiments, the reactor feed can include ethanol. The ethanol can be at a concentration of less than about 20 wt. %. The ethanol can be at a concentration of greater than about 10 wt. %. The ethanol can be at a concentration of greater than about 5 wt. %. The ethanol can be at a concentration of greater than about 2 wt. %.

In some embodiments, the reactor feed can include ethanol, water, and the $C_3$-$C_6$ alcohols. The mixture of $C_3$-$C_6$ alcohols can include at least one of 2-methyl-1-butanol (active amyl alcohol), isoamyl alcohol (isopentanol), isobutyl alcohol, and n-propyl alcohol, propanol, butanol, pentanol, or hexanol. The mixture of $C_3$-$C_6$ alcohols can include two or more of 2-methyl-1-butanol (active amyl alcohol), isoamyl alcohol (isopentanol), isobutyl alcohol, and n-propyl alcohol, propanol, butanol, pentanol, or hexanol.

The mixture of $C_3$-$C_6$ alcohols can be contacted with the mixed oxide catalyst at a temperature within the range of about 300° C. to about 600° C., about 400° C. to about 500° C., about 415° C. to about 470° C., or about 425° C. to about 445° C. The mixture of $C_3$-$C_6$ alcohols can be contacted with the mixed oxide catalyst at a weight hourly space velocity range of about 0.1 hr$^{-1}$ to about 2.5 hr$^{-1}$, about 2.0 hr$^{-1}$, or about 1.5 hr$^{-1}$.

The ketone formation reaction temperature of fusel oil mixtures consisting of branched and/or linear $C_2$-$C_5$ alcohols can be from 400° C. to 500° C., with reaction pressures ranging from 0-100 psig.

The ketone formation reaction can be performed in continuous mode for mass production of ketones. The continuous mode can be operated by using a fixed bed reactor, and reactant flows can be upward or downward.

The aldehyde formation reaction temperature of fusel oil mixtures consisting of branched and/or linear $C_2$-$C_5$ alcohols can be from 400° C. to 500° C., with reaction pressures ranging from 0-100 psig.

The aldehyde formation reaction can be performed in continuous mode for mass production of ketones. The continuous mode can be operated by using a fixed bed reactor, and reactant flows can be upward or downward.

The isoprene formation reaction temperature of the $C_5$ aldehyde mixture consisting of 3-methylbutanal and 2-methylbutanal is from 300° C. to 500° C., with reaction pressures ranging from 0-100 psig.

The isoprene formation reaction is performed in continuous mode for mass production of isoprene. The continuous mode is operated by using a fixed bed reactor, and reactant flows can be upward or downward.

The isoamylene formation reaction temperature of fusel oil mixtures consisting of branched and/or linear $C_2$-$C_5$ alcohols is from 250° C. to 400° C., with reaction pressures ranging from 0-100 psig.

The isoamylene formation reaction is performed in continuous mode for mass production of olefins. The continuous mode can be operated by using a fixed bed reactor, and reactant flows can be upward or downward.

Fusel oil mixture (ie. $C_2$-$C_5$ alcohol) single pass conversion in the ketone formation reaction is typically higher than about 90%.

Fusel oil mixture (ie. $C_2$-$C_5$ alcohol) single pass conversion in the acceptorless aldehyde formation reaction is typically higher than about 70%.

Aldehyde mixture (ie. 3-methylbutanal and 2-methylbutanal at 70/30 ratio) single pass conversion in the isoprene formation reaction is typically higher than about 20%.

Fusel oil mixture (ie. $C_2$-$C_5$ alcohol) single pass conversion in the isoamylene formation reaction is typically higher than about 90%.

One skilled in the art will immediately recognize the similarity of the reaction conditions and parameters for the aforementioned reactions, and how a multi-purpose plant configuration would be suitable to allow production of the various renewable chemicals depending upon market conditions in order to maximize profitability and plant utilization.

Granular or extruded catalysts are suitable for the reactions even though no specific size and morphology are mandatory. Catalyst with a size greater than 0.1 mm is more suitable, and the size of 0.2-1.0 mm is most suitable for the operation ability and low pressure drop.

Reactor Set-Up

The fusel oil upgrading options were carried out at 300-500° C., via a fixed bed reactor, containing 2.9 g, 5.0 g, or 15 g of specified catalyst, and flowing preheated (160° C.) vaporized fusel oils in a downward flow over the fixed catalyst bed while in some cases co-feeding nitrogen. The flow rates of fusel oils and/or ethanol were controlled by Teledyne model 500D syringe pumps, and the flow rates were adjusted to obtain the targeted olefin WHSV (weight hourly space velocity). The internal reaction temperature was maintained constant via a Lindberg Blue M furnace as manufactured by Thermo-Scientific. Fusel oil conversion and selectivity was calculated by analysis of the liquid phase reactor effluent by GC for organic and water content, and comparing mass accountability fed versus liquid mass collected.

EXAMPLES

Example 1a: Impregnated $Zn_v/Mg_w/Mn_y/Zr_z$ (V:W:Y:Z) (Nominal Metal Mol % Ratio 1/2/5/18, Respectively) Catalyst Preparation Zn/Mg/Mn/Zr catalyst was prepared by incipient wetness technique. The precursor metal salts (Sigma Aldrich): 0.308 g zinc nitrate hexahydrate and 0.43 g of magnesium acetate tetrahydrate were added and dissolved in deionized water (3.8 ml). Upon salt dissolution, the solution was added in dropwise fashion to 3 g manganese/zirconium (nominal metal mol % ratio 1/4) support. The resulting mixed metal oxide was manually mixed to assure complete wetting, and the resulting impregnated catalyst was dried at 160° C. for 1 hr, and afterwards calcined at 500° C. for 4 hrs.

Example 1b: Boron Impregnated Niobium/Alumina Catalyst Preparation

Nb/alumina+3.7 wt % boron catalyst was prepared by incipient wetness technique as described. 0.63 g boric acid (Sigma Aldrich) was added to deionized water (4.0 g) and gently heated to dissolve. Upon boric acid dissolution, the solution was added in dropwise fashion to 3 g niobium/alumina (9 wt. % niobium content) support. The resulting impregnated mixed metal oxide was manually mixed to assure complete wetting, and the resulting impregnated catalyst was dried at 160° C. for 1 hr, and afterwards calcined at 550° C. for 4 hrs.

Example 1c: Boron and Phosphor Impregnated Zeolite Catalyst Preparation

Zeolite type ZSM-5 (Zeolyst CBV-5524H+2.7 wt. % boron+3.5 wt. % phosphor catalyst was prepared by incipient wetness technique as described. 0.47 g boric acid (Sigma Aldrich) and 0.40 g phosphoric acid (85 wt. %) was added to deionized water (3.6 g) and gently heated to dissolve. Upon mixed acid dissolution, the solution was added in dropwise fashion to 3 g zeolite support. The resulting impregnated zeolite was manually mixed to assure complete wetting, and the resulting impregnated catalyst was dried at 160° C. for 1 hr, and afterwards calcined at 550° C. for 4 hrs.

TABLE 1

Reaction Conditions: T = 440° C., WHSV = 2.0; Catalyst - Quaternary metal oxide (Zn/Mg/Mn/Zr @ relative metal ratio 1/2/5/18); Refined Fusel Oil Composition: 1 wt. % Ethanol, 3 wt. % Isobutanol, 80 wt. % 3-Methyl-1-butanol, 13 wt. % 2-Methyl-1-butanol, 3 wt. % Water; Liquid Mass accountability (Mass Out/Mass In) = 60 wt. %

| Reactor Effluent Composition | Wt. % of Total: |
|---|---|
| $C_5$ aldehydes | 21 |
| Methyl isobutyl ketone | 9 |
| $C_6$-$C_7$ ketones | 8 |
| Di-isobutyl ketone | 40 |
| $C_9$+ ketones | 9 |
| $C_2$-$C_5$ olefins | 3 |
| Hydrogen | 3.0 eq |

TABLE 2

Reaction Conditions: T = 435° C., WHSV = 2.0; Catalyst - Quaternary metal oxide (Zn/Cu/Mn/Zr @ relative metal ratio 1/2/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 64 wt. %

| Reactor Effluent Composition | Wt. % of Total: |
|---|---|
| $C_5$ aldehydes | 28 |
| Methyl isobutyl ketone | 15 |
| $C_6$-$C_7$ ketones | 4 |
| Di-isobutyl ketone | 18 |
| Valeric acid, Isopentyl ester | 10 |

TABLE 2-continued

Reaction Conditions: T = 435° C., WHSV = 2.0; Catalyst - Quaternary metal oxide (Zn/Cu/Mn/Zr @ relative metal ratio 1/2/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 64 wt. %

| Reactor Effluent Composition | Wt. % of Total: |
|---|---|
| $C_9$+ ketones | 2 |
| $C_2$-$C_5$ olefins | 11 |

TABLE 3

Reaction Conditions: T = 470° C., WHSV = 2.0; Catalyst - Quaternary metal oxide (Zn/Al/Si/Zr @ relative metal ratio 1/2/2/11); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 32 wt. %

| Reactor Effluent Composition | Wt. % of Total: |
|---|---|
| $C_5$ aldehydes | 12 |
| Methyl isobutyl ketone | 23 |
| $C_6$-$C_7$ ketones | 4 |
| Di-isobutyl ketone | 28 |
| Valeric acid, Isopentyl ester | <1 |
| $C_9$+ ketones | 2 |
| $C_2$-$C_5$ Olefins | 17 |

TABLE 4

Reaction Conditions: T = 425° C., WHSV = 1.5; Catalyst - Quaternary metal oxide (Zn/Mg/Mn/Zr @ relative metal ratio 1/4/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 61 wt. %

| Reactor Effluent Composition | Wt. % of Total: |
|---|---|
| $C_5$ aldehydes | 23 |
| Methyl isobutyl ketone | 25 |
| $C_6$-$C_7$ ketones | 4 |
| Di-isobutyl ketone | 25 |
| Valeric acid, Isopentyl ester | 9 |
| $C_9$+ ketones | 3 |
| $C_2$-$C_5$ olefins | 1 |

TABLE 5

Reaction Conditions: T = 445° C., WHSV = 1.5; Catalyst - Quaternary metal oxide (Zn/Mg/Mn/Zr @ relative metal ratio 1/4/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 54 wt. %

| Reactor Effluent Composition | Wt. % of Total: |
|---|---|
| $C_5$ aldehydes | 1 |
| Methyl isobutyl ketone | 36 |
| $C_6$-$C_7$ ketones | 8 |
| Di-isobutyl ketone | 46 |
| Valeric acid, Isopentyl ester | 0.7 |
| C9+ ketones | 2 |
| $C_2$-$C_5$ olefins | <1 |

TABLE 6

Reaction Conditions: T = 425° C., WHSV = 1.5; Catalyst - Quaternary metal oxide (Zn/Mg/Mn/Zr @ relative metal ratio 1/4/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 72 wt.

| % Reactor Effluent Composition | Wt. % of Total: |
|---|---|
| $C_5$ aldehydes | 29 |
| Methyl isobutyl ketone | 21 |
| $C_6$-$C_7$ ketones | 2 |
| Di-isobutyl ketone | 9 |
| Valeric acid, Isopentyl ester | 6 |
| $C_9$+ ketones | 3 |
| $C_2$-$C_5$ olefins | <1 |

TABLE 7

Reaction Conditions: T = 445° C., WHSV = 1.5; Catalyst - Quaternary metal oxide (Zn/Mg/Mn/Zr @ relative metal ratio 1/4/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 44 wt. %

| Reactor Effluent Composition | Wt. % of Total: |
|---|---|
| $C_5$ aldehydes | 3 |
| Methyl isobutyl ketone | 50 |
| $C_6$-$C_7$ ketones | 12 |
| Di-isobutyl ketone | 31 |
| Valeric acid, Isopentyl ester | <1 |
| $C_9$+ ketones | 2 |
| $C_2$-$C_5$ Olefins | <1 |

TABLE 8

Reaction Conditions: T = 415° C., WHSV = 1.5; Catalyst - Quaternary metal oxide (Zn/Mg/Mn/Zr @ relative metal ratio 2/1/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 69 wt. %

| Reactor Effluent Composition | Wt. % of Total: |
|---|---|
| $C_5$ aldehydes | 26 |
| Methyl isobutyl ketone | 35 |
| $C_6$-$C_7$ ketones | 3 |
| Di-isobutyl ketone | 18 |
| Valeric acid, Isopentyl ester | 10 |
| $C_9$+ ketones | 2 |
| $C_2$-$C_5$ olefins | <1 |

TABLE 9

Reaction Conditions: T = 430° C., WHSV = 2.0; Catalyst - Quaternary metal oxide (Zn/Mg/Mn/Zr @ relative metal ratio 2/2/5/18); Crude Fusel Oil Composition: 10.6 wt. % Ethanol, 1.3 wt. % Isobutanol, 68.2 wt. % 3-Methyl-1-butanol, 13 wt. % 2-Methyl-1-butanol, 7 wt. % Water; Liquid Mass accountability (Mass Out/Mass In) = 57 wt. %

| Reactor Effluent Composition | Wt. % of Total: |
|---|---|
| $C_5$ aldehydes | 21 |
| Methyl isobutyl ketone | 32 |
| $C_6$-$C_7$ ketones | 6 |
| Di-isobutyl ketone | 26 |
| Valeric Acid, Isopentyl ester | 6 |
| $C_9$+ ketones | 4 |
| $C_2$-$C_5$ olefins | <1 |

TABLE 10

Reaction Conditions: T = 445° C., WHSV = 1.5; Catalyst - Binary metal oxide (Mn/Zr @ relative metal ratio 5/18); Crude Fusel Oil Composition: 8.4 wt. % Ethanol, 12 wt. % Isobutanol, 50 wt. % 3-Methyl-1-butanol, 15 wt. % 2-Methyl-1-butanol, 12 wt. % Water; Liquid Mass accountability (Mass Out/Mass In) = 51 wt. %

| Reactor Effluent Composition | Wt. % of Total: |
|---|---|
| $C_5$ aldehydes | nd |
| Methyl isobutyl ketone | 23 |
| $C_6$-$C_7$ ketones | 20 |
| Di-isobutyl ketone | 32 |
| Valeric Acid, Isopentyl ester | <1 |
| $C_9$+ ketones | 2 |
| $C_2$-$C_5$ olefins | <1 |

TABLE 11

Reaction Conditions: T = 445° C., WHSV = 1.5; Catalyst - Tertiary metal oxide (Mg/Mn/Zr @ relative metal ratio 2/5/18); Crude Fusel Oil Composition: 8.4 wt. % Ethanol, 12 wt. % Isobutanol, 50 wt. % 3-Methyl-1-butanol, 15 wt. % 2-Methyl-1-butanol, 12 wt. % Water; Liquid Mass accountability (Mas Out/Mass In) = 52 wt. %

| Reactor Effluent Composition | Wt. % of Total: |
|---|---|
| $C_5$ aldehydes | 2 |
| Methyl isobutyl ketone | 13 |
| $C_6$-$C_7$ ketones | 26 |
| Di-isobutyl ketone | 25 |
| Valeric acid, Isopentyl ester | <1 |
| $C_9$+ ketones | 2 |
| $C_2$-$C_5$ olefins | 2 |

TABLE 12

Reaction Conditions: T = 440° C., WHSV = 2.0; Catalyst - Tertiary metal oxide (Zn/Mn/Zr @ relative metal ratio 1/5/18); Crude Fusel Oil Composition: 8.4 wt. % Ethanol, 12 wt. % Isobutanol, 50 wt. % 3-Methyl-1-butanol, 15 wt. % 2-Methyl-1-butanol, 12 wt. % Water; Liquid Mass accountability (Mass Out/Mass In) = 64 wt. %

| Reactor Effluent Composition | Wt. % of Total: |
|---|---|
| $C_5$ aldehydes | 20 |
| Methyl isobutyl ketone | 21 |
| $C_6$-$C_7$ ketones | 23 |
| Di-isobutyl ketone | 15 |
| Valeric Acid, Isopentyl ester | 5 |
| $C_9$+ ketones | 3 |
| $C_2$-$C_5$ olefins | <1 |

TABLE 13

Reaction Conditions: T = 440° C., WHSV = 2.0; Catalyst - Tertiary metal oxide (Zn/Mn/Zr @ relative metal ratio 2/5/18); refined Fusel Oil Composition: 1 wt. % Ethanol, 2.6 wt. % Isobutanol, 81 wt. % 3-Methyl-1-butanol, 14 wt. % 2-Methyl-1-butanol, 1 wt. % Water; Liquid Mass accountability (Mass Out/Mass In) = 76 wt. %

| Reactor Effluent Composition | Wt. % of Total: |
|---|---|
| $C_5$ aldehydes | 33 |
| Methyl isobutyl ketone | 7 |
| $C_6$-$C_7$ ketones | 5 |
| Di-isobutyl ketone | 28 |
| Valeric acid, Isopentyl ester | 9 |
| $C_9$+ ketones | 3 |
| $C_2$-$C_5$ olefins | <1 |

TABLE 14

Reaction Conditions: T = 440° C., WHSV = 2.0; Catalyst - Binary metal oxide (Zn/Zr @ relative metal ratio 3/11); refined Fusel Oil Composition: 1 wt. % Ethanol, 2.6 wt. % Isobutanol, 81 wt. % 3-Methyl-1-butanol, 14 wt. % 2-Methyl-1-butanol, 1 wt. % Water; Liquid Mass accountability (Mass Out/Mass In) = 76 wt. %

| Reactor Effluent Composition | Wt. % of Total: |
|---|---|
| $C_5$ aldehydes | 50 |
| Methyl isobutyl ketone | 5 |
| $C_6$-$C_7$ ketones | 3 |
| Di-isobutyl ketone | 11 |
| Valeric Acid, Isopentyl ester | 18 |
| $C_9$+ ketones | 2 |
| $C_2$-$C_5$ Olefins | <1 |

TABLE 15

Reaction Conditions: T = 440° C., WHSV = 2.0; Catalyst - Metal oxide (tetragonal $ZrO_2$ @ 100%); Refined Fusel Oil Composition: 1 wt. % Ethanol, 2.6 wt. % Isobutanol, 81 wt. % 3-Methyl-1-butanol, 14 wt. % 2-Methyl-1-butanol, 1 wt. % Water; Liquid Mass accountability (Mass Out/Mass In) = 38 wt. %

| Reactor Effluent Composition | Wt. % of Total: |
|---|---|
| $C_5$ aldehydes | <1 |
| Methyl isobutyl ketone | nd |
| $C_6$-$C_7$ ketones | <2 |
| Di-isobutyl ketone | 8 |
| Valeric acid, Isopentyl ester | <1 |
| $C_9$+ ketones | <1 |
| $C_2$-$C_5$ olefins | 72 |

TABLE 16

Reaction Conditions: T = 440° C., WHSV = 2.0; Catalyst - Tertiary metal oxide (Zn/Mn/Zr @ relative metal ratio 1/5/18); Crude Fusel Oil Composition: 8.4 wt. % Ethanol, 12 wt. % Isobutanol, 50 wt. % 3-Methyl-1-butanol, 15 wt. % 2-Methyl-1-butanol, 12 wt. % Water; Liquid Mass accountability (Mass Out/Mass In) = 63 wt. %

| Reactor Effluent Composition | Wt. % of Total: |
|---|---|
| $C_5$ aldehydes | 16 |
| Methyl isobutyl ketone | 17 |
| $C_6$-$C_7$ ketones | 20 |
| Di-isobutyl ketone | 24 |
| Valeric acid, Isopentyl ester | 3 |
| $C_9$+ ketones | 3 |
| $C_2$-$C_5$ olefins | <1 |

TABLE 17

Reaction Conditions: T = 455° C., WHSV = 2.0; Catalyst - Metal oxide (ZnO @ 100%); Crude Fusel Oil Composition: 10.6 wt. % Ethanol, 1.3 wt. % Isobutanol, 68 wt. % 3-Methyl-1-butanol, 13 wt. % 2-Methyl-1-butanol, 7 wt. % Water; Liquid Mass accountability (Mass Out/Mass In) = 80 wt. %

| Reactor Effluent Composition | Wt. % of Total: |
|---|---|
| $C_5$ aldehydes | 48 |
| Methyl isobutyl ketone | 10 |
| $C_6$-$C_7$ ketones | 5 |
| Di-isobutyl ketone | <1 |
| Valeric acid, Isopentyl ester | 2 |
| $C_9$+ ketones | <1 |
| $C_2$-$C_5$ olefins | <1 |

TABLE 18

Reaction Conditions: T = 415° C., WHSV = 2.0; Catalyst - Binary metal oxide (Zn/Zr @ relative metal ratio 1/8; co-precipitated) Crude Fusel Oil Composition: 10.6 wt. % Ethanol, 1.3 wt. % Isobutanol, 68 wt. % 3-Methyl-1-butanol, 13 wt. % 2-Methyl-1-butanol, 7 wt. % Water; Liquid Mass accountability (Mass Out/Mass In) = 63 wt. %

| Reactor Effluent Composition | Wt. % of Total: |
|---|---|
| $C_5$ aldehydes | 39 |
| Methyl isobutyl ketone | 10 |
| $C_6$-$C_7$ ketones | 2 |
| Di-isobutyl ketone | 2 |
| Valeric acid, Isopentyl ester | 18 |
| $C_9$+ ketones | <1 |
| $C_2$-$C_5$ olefins | 10 |

TABLE 19

Reaction Conditions: T = 435° C., WHSV = 2.0; Catalyst - Binary metal oxide (Zn/Zr @ relative metal ratio 3/11) Crude Fusel Oil Composition: 10.6 wt. % Ethanol, 1.3 wt. % Isobutanol, 68 wt. % 3-Methyl-1-butanol, 13 wt. % 2-Methyl-1-butanol, 7 wt. % Water; Liquid Mass accountability (Mass Out/Mass In) = 78 wt. %

| Reactor Effluent Composition | Wt. % of Total: |
|---|---|
| $C_5$ aldehydes | 48 |
| Methyl isobutyl ketone | 16 |
| $C_6$-$C_7$ ketones | 2 |
| Di-isobutyl ketone | 6 |
| Valeric acid, Isopentyl ester | 17 |
| $C_9$+ ketones | 2 |
| $C_2$-$C_5$ olefins | <1 |

TABLE 20

Reaction Conditions: T = 455° C., WHSV = 2.0; Catalyst - Tertiary metal oxide (Zn/Mg/Zr @ relative metal ratio 1/2/24) Crude Fusel Oil Composition: 10.6 wt. % Ethanol, 1.3 wt. % Isobutanol, 68 wt. % 3-Methyl-1-butanol, 13 wt. % 2-Methyl-1-butanol, 7 wt. % Water; Liquid Mass accountability (Mass Out/Mass In) = 71%

| Reactor Effluent Composition | Wt. % of Total: |
|---|---|
| $C_5$ aldehydes | 42 |
| Methyl isobutyl ketone | 22 |
| $C_6$-$C_7$ ketones | 2 |
| Di-isobutyl ketone | 13 |
| Valeric acid, Isopentyl ester | 8 |
| $C_9$+ ketones | 2 |
| $C_2$-$C_5$ olefins | <1 |

TABLE 21

Reaction Conditions: T = 420 C., WHSV = 1.5; Catalyst - Quaternary metal oxide (Zn/Mg/Mn/Zr @ relative metal ratio 1/2/5/18); Fusel Oil + Ethanol Mixture Composition: 48.7 wt. % Ethanol, 0.8 wt. % Isobutanol, 39.2 wt. % 3-Methyl-1-butanol, 7.5 wt. % 2-Methyl-1-butanol, 3.8 wt. % Water; Liquid Mass accountability (Mass Out/Mass In) = 53 wt. %

| Reactor Effluent Composition | Wt. % of Total: |
|---|---|
| Acetone | 5 |
| $C_5$ aldehydes | 3 |
| 2-pentanone | 6 |
| Methyl isobutyl ketone | 38 |
| sec-butyl methyl ketone | 6 |
| Propyl isobutyl ketone | 3 |
| 6-methyl-2-heptenone | 3 |

TABLE 21-continued

Reaction Conditions: T = 420 C., WHSV = 1.5; Catalyst - Quaternary metal oxide (Zn/Mg/Mn/Zr @ relative metal ratio 1/2/5/18); Fusel Oil + Ethanol Mixture Composition: 48.7 wt. % Ethanol, 0.8 wt. % Isobutanol, 39.2 wt. % 3-Methyl-1-butanol, 7.5 wt. % 2-Methyl-1-butanol, 3.8 wt. % Water; Liquid Mass accountability (Mass Out/Mass In) = 53 wt. %

| Reactor Effluent Composition | Wt. % of Total: |
|---|---|
| 6-methyl-2-heptanone | 6 |
| Di-isobutyl ketone | 10 |
| m-cresol | 4 |

TABLE 22

Reaction Conditions: T = 410° C., WHSV = 1.5; Catalyst - Quaternary metal oxide (Zn/Mg/Mn/Zr @ relative metal ratio 1/2/5/18); Fusel Oil + Ethanol Mixture Composition: 48.7 wt. % Ethanol, 0.8 wt. % Isobutanol, 39.2 wt. % 3-Methyl-1-butanol, 7.5 wt. % 2-Methyl-1-butanol, 3.8 wt. % Water; Liquid Mass accountability (Mass Out/Mass In) = 53 wt. %

| Reactor Effluent Composition | Wt. % of Total: |
|---|---|
| Acetone | 4 |
| $C_5$ aldehydes | 11 |
| 2-pentanone | 4 |
| Methyl isobutyl ketone | 38 |
| sec-butyl methyl ketone | 5 |
| Propyl isobutyl ketone | 2 |
| 6-methyl-2-heptenone | 3 |
| 6-methyl-2-heptanone | 6 |
| Di-isobutyl ketone | 5 |
| m-cresol | 6 |

TABLE 23

Reaction Conditions: T = 395° C., WHSV = 1.5; Catalyst - Quaternary metal oxide (Zn/Mg/Mn/Zr @ relative metal ratio 1/2/5/18); Fusel Oil + Ethanol Mixture Composition: 48.7 wt. % Ethanol, 0.8 wt. % Isobutanol, 39.2 wt. % 3-Methyl-1-butanol, 7.5 wt. % 2-Methyl-1-butanol, 3.8 wt. % Water; Liquid Mass accountability (Mass Out/Mass In) = 58 wt. %

| Reactor Effluent Composition | Wt. % of Total: |
|---|---|
| Acetone | 4 |
| $C_5$ Aldehydes | 18 |
| 2-pentanone | 5 |
| Methyl isobutyl ketone | 20 |
| sec-butyl methyl ketone | 3 |
| Propyl isobutyl ketone | 1 |
| 6-methyl-2-heptenone | 3 |
| 6-methyl-2-heptanone | 6 |
| Di-isobutyl ketone | 1 |
| m-cresol | 7 |

TABLE 24

Reaction Conditions: T = 480° C., WHSV = 1.5; Catalyst - Quaternary metal oxide (Zn/Mg/Mn/Zr @ relative metal ratio 1/2/5/18); Fusel Oil + Ethanol Mixture Composition: 29.7 wt. % Ethanol, 2.2 wt. % n-propanol, 6.8 wt. % Isobutanol, 37.5 wt. % 3-Methyl-1-butanol, 11.9 wt. % 2-Methyl-1-butanol, 12 wt. % Water; Liquid Mass accountability (Mass Out/Mass In) = 68 wt. %

| Reactor Effluent Composition | Wt. % of Total: |
|---|---|
| Acetone | 4 |
| Methyl ethyl ketone | 2 |
| $C_5$ aldehydes | 7 |
| 2-pentanone | 3 |

TABLE 24-continued

Reaction Conditions: T = 480° C., WHSV = 1.5; Catalyst - Quaternary metal oxide (Zn/Mg/Mn/Zr @ relative metal ratio 1/2/5/18); Fusel Oil + Ethanol Mixture Composition: 29.7 wt. % Ethanol, 2.2 wt. % n-propanol, 6.8 wt. % Isobutanol, 37.5 wt. % 3-Methyl-1-butanol, 11.9 wt. % 2-Methyl-1-butanol, 12 wt. % Water; Liquid Mass accountability (Mass Out/Mass In) = 68 wt. %

| Reactor Effluent Composition | Wt. % of Total: |
|---|---|
| Methyl isobutyl ketone | 41 |
| sec-butyl methyl ketone | 10 |
| Propyl isobutyl ketone | 4 |
| 6-methyl-2-heptenone | 7 |
| 6-methyl-2-heptanone | 2 |
| Di-isobutyl ketone | 7 |

TABLE 25

Reaction Conditions: T = 390° C., WHSV = 2.4; Catalyst - ZSM5 (CBV-5524H$^+$) doped with 1.6 wt. % Boron; Crude Aldehyde Composition: 79 wt. % 3-methyl-butanal, 20 wt. % 2-methyl-butanal, 1 wt. % Water; Liquid Mass accountability (Mass Out/Mass In) = 95.2 wt. %

| Reactor Effluent Composition | Wt. % of Total: |
|---|---|
| isobutane | 1.3 |
| isobutylene | 6.4 |
| 3-methyl-1-butene | 1.1 |
| isoprene | 16.8 |
| 2-methyl-2-butene | 2.9 |
| 3-methyl-butanal | 59.6 |
| 2-methyl-butanal | 5.0 |
| 2-pentanone | 1.5 |
| 3-pentanone | 1.6 |
| 3/2-methyl-butanoic acid | 1.5 |

TABLE 26

Reaction Conditions: T = 380° C., WHSV = 2.4; Catalyst - Niobium (10 wt. %) on Alumina; Crude Aldehyde Composition: 70 wt. % 3-methyl-butanal, 30 wt. % 2-methyl-butanal, 1 wt. % Water; Liquid Mass accountability (Mass Out/Mass In) = 83.3 wt. %

| Reactor Effluent Composition | Wt. % of Total: |
|---|---|
| isobutane | 0.3 |
| isobutylene | 2.6 |
| linear butenes | 0.5 |
| 3-methyl-1-butene | 5.2 |
| 2-methyl-1-butene | 3.9 |
| isoprene | 19.7 |
| 2-methyl-2-butene | 10.0 |
| 3-methyl-butanal | 29.8 |
| 2-methyl-butanal | 6.8 |
| methyl isopropyl ketone | 2.8 |
| 3/2-methyl-butanoic acid | 4.0 |
| $C_9+$ aromatics | 12.0 |

TABLE 27

Reaction Conditions: T = 380° C., WHSV = 2.4; Catalyst - Niobium (10 wt. %) on Alumina; Crude Aldehyde Composition: 65 wt. % 3-methyl-butanal, 35 wt. % 2-methyl-butanal, 1 wt. % Water; Liquid Mass accountability (Mass Out/Mass In) = 85.8 wt. %

| Reactor Effluent Composition | Wt. % of Total: |
|---|---|
| isobutane | 0.5 |
| isobutylene | 3.9 |

TABLE 27-continued

Reaction Conditions: T = 380° C., WHSV = 2.4; Catalyst - Niobium (10 wt. %) on Alumina; Crude Aldehyde Composition: 65 wt. % 3-methyl-butanal, 35 wt. % 2-methyl-butanal, 1 wt. % Water; Liquid Mass accountability (Mass Out/Mass In) = 85.8 wt. %

| Reactor Effluent Composition | Wt. % of Total: |
|---|---|
| linear butenes | 0.7 |
| 3-methyl-1-butene | 4.8 |
| 2-methyl-1-butene | 5.2 |
| isoprene | 21.0 |
| 2-methyl-2-butene | 13.1 |
| 3-methyl-butanal | 18.9 |
| 2-methyl-butanal | 4.9 |
| methyl isopropyl ketone | 3.9 |
| 3/2-methyl-butanoic acid | 4.9 |
| $C_9$+ aromatics | 17.0 |

TABLE 28

Reaction Conditions: T = 450° C., WHSV = 2.4 with water co-fed; Catalyst - Zirconium oxide doped with Boron and Phosphorus; Crude Aldehyde Composition: 65 wt. % 3-methyl-butanal, 35 wt. % 2-methyl-butanal, 1 wt. % Water; Liquid Mass accountability (Mass Out/Mass In) = 98.9 wt. %

| Reactor Effluent Composition | Wt. % of Total: |
|---|---|
| isobutane | 0.3 |
| isobutylene | 3.2 |
| linear butenes | 0.7 |
| 3-methyl-1-butene | 0.2 |
| 2-methyl-1-butene | 0.5 |
| isoprene | 27.6 |
| 2-methyl-2-butene | 1.0 |
| 3-methyl-butanal | 52.5 |
| 2-methyl-butanal | 8.8 |
| methyl isopropyl ketone | 1.4 |
| 3/2-methyl-butanoic acid | 1.0 |
| $C_9$+ aromatics | nd |

TABLE 29

Reaction Conditions: T = 430° C., WHSV = 2.4; Catalyst - Zeolite CBV-5524 doped with 3.7 wt. % Boron; Crude Aldehyde Feed Composition: 80 wt. % 3-methyl-butanal, 20 wt. % 2-methyl-butanal, 1 wt. % Water; Liquid Mass accountability (Mass Out/Mass In) = 90.9 wt. %

| Reactor Effluent Composition | Wt. % of Total: |
|---|---|
| isobutane | 0.6 |
| isobutylene | 9.6 |
| linear butenes | 1.5 |
| 3-methyl-1-butene | nd |
| 2-methyl-1-butene | 0.6 |
| isoprene | 18.5 |
| 2-methyl-2-butene | 1.3 |
| 3-methyl-butanal | 55.4 |
| 2-methyl-butanal | 4.0 |
| methyl isopropyl ketone | 1.3 |
| 3/2-methyl-butanoic acid | 2.0 |
| $C_9$+ aromatics | nd |

TABLE 30

Reaction Conditions: T = 395° C., WHSV = 2.4; Catalyst - Zeolite CBV-5524 doped with 2.7 wt. % boron and 3.5 wt. % Phosphor; Crude Aldehyde Feed Composition: 68 wt. % 3-methyl-butanal, 32 wt. % 2-methyl-butanal, 1 wt. % Water; Liquid Mass accountability (Mass Out/Mass In) = 97.1 wt. %

| Reactor Effluent Composition | Wt. % of Total: |
|---|---|
| isobutane | 0.8 |
| isobutylene | 6.6 |
| linear butenes | 1.6 |
| 3-methyl-1-butene | nd |
| 2-methyl-1-butene | 0.5 |
| isoprene | 20.2 |
| 2-methyl-2-butene | 1.4 |
| 3-methyl-butanal | 50.0 |
| 2-methyl-butanal | 8.0 |
| methyl isopropyl ketone | 1.3 |
| 3/2-methyl-butanoic acid | 2.0 |
| $C_9$+ aromatics | nd |

TABLE 31

Reaction Conditions: T = 385° C., WHSV = 2.4; Catalyst - Niobium (10 wt. %) on Alumina doped with 3.7 wt. % Boron; Crude Aldehyde Feed Composition: 70 wt. % 3-methyl-butanal, 30 wt. % 2-methyl-butanal, 1 wt. % Water; Liquid Mass accountability (Mass Out/Mass In) = 90 wt. %

| Reactor Effluent Composition | Wt. % of Total: |
|---|---|
| isobutane | 0.3 |
| isobutylene | 3.0 |
| linear butenes | 0.5 |
| 3-methyl-1-butene | 1.8 |
| 2-methyl-1-butene | 3.4 |
| isoprene | 16.3 |
| 2-methyl-2-butene | 8.8 |
| 3-methyl-butanal | 47.3 |
| 2-methyl-butanal | 8.8 |
| methyl isopropyl ketone | 2.2 |
| 3/2-methyl-butanoic acid | 2.0 |
| $C_9$+ aromatics | 4.2 |

The foregoing specific examples are intended to be illustrative of the invention and should not be construed as limiting the scope of the invention as defined by appended claims.

The foregoing detailed description has been given for clearness of understanding only and no unnecessary limitations should be understood there from as modifications will be obvious to those skilled in the art.

The disclosures, including the claims, figures and/or drawings, of each and every patent, patent application, and publication cited herein are hereby incorporated herein by reference in their entireties.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A process for preparing a renewable chemical, comprising:

(a) feeding to a reactor a reactor feed comprising a mixture of $C_3$-$C_6$ alcohols at a concentration of at least about 75 wt. %; and (b) contacting the mixture of $C_3$-$C_6$ alcohols with a mixed oxide catalyst in the reactor, the mixed oxide catalyst having a formula $Zn_v/Mg_w/Cu_x/Mn_y/Zr_z$, whereby the mixture is converted to at least one renewable chemical at a yield of at least about 25 wt. %, wherein either (i) V is 1 to 10, W is 1 to 50, X is 0 to 20, Y is 1 to 50, Z is 1 to 180, wherein atomic ratios of each of V and W, relative to Y or Z, are each 1 to 10, and wherein atomic ratios for Y and Z relative to each other is 1 to 16; or (ii) V is 0 to 10, W is 0 to 50, X is 0 to 20, Y is 1 to 50, Z is 1 to 180, wherein atomic ratios of each of V and W, relative to Y or Z, are each 0 to 10, and wherein atomic ratios for Y and Z relative to each other is 3 to 6.

2. The process of claim 1, wherein the atomic ratios for Y and Z relative to each other is 1 to 6.

3. The process of claim 1, wherein the atomic ratios for Y and Z relative to each other is 2 to 16.

4. The process of claim 1, wherein the at least one renewable chemical is methyl isobutyl ketone (MIBK).

5. The process of claim 4, wherein the yield of the methyl isobutyl ketone (MIBK) is at least about 35%.

6. The process of claim 5, wherein the yield of the methyl isobutyl ketone (MIBK) is at least about 45%.

7. The process of claim 1, wherein the at least one renewable chemical is di-isobutyl ketone (DIBK).

8. The process of claim 7, wherein the yield of the di-isobutyl ketone (DIBK) is at least about 35%.

9. The process of claim 8, wherein the yield of the di-isobutyl ketone (DIBK) is at least about 45%.

10. The process of claim 1, wherein the at least one renewable chemical is a $C_5$ aldehyde.

11. The process of claim 10, wherein the yield of the $C_5$ aldehyde is at least about 35%.

12. The process of claim 11, wherein the yield of the $C_5$ aldehyde is at least about 45%.

13. The process of claim 1, wherein the at least one renewable chemical is isoprene.

14. The process of claim 13, wherein the yield of the isoprene is at least about 35%.

15. The process of claim 14, wherein the yield of the isoprene is at least about 45%.

16. The process of claim 1, wherein the at least one renewable chemical is isoamylene.

17. The process of claim 16, wherein the yield of the isoamylene is at least about 35%.

18. The process of claim 17, wherein the yield of the isoamylene is at least about 45%.

19. The process of claim 1, further comprising step (c) of recovering the at least one renewable chemical.

20. The process of claim 19, wherein the renewable chemical recovered in step (c) is methyl isobutyl ketone (MIBK).

21. The process of claim 19, wherein the renewable chemical recovered in step (c) is di-isobutyl ketone (DIBK).

22. The process of claim 19, wherein the at least one renewable chemical recovered in step (c) is a Cs aldehyde.

23. The process of claim 19, wherein the at least one renewable chemical recovered in step (c) is isoprene.

24. The process of claim 19, wherein the at least one renewable chemical recovered in step (c) is isoamylene.

25. The process of claim 1, wherein the mixture of $C_3$-$C_6$ alcohols is bio-based.

26. The process of claim 25, wherein at least about 60 wt. % of the mixture of $C_3$-$C_6$ alcohols is derived from a non-petroleum feedstock.

27. The process of claim 26, wherein at least about 70 wt. % of the mixture of $C_3$-$C_6$ alcohols is derived from a non-petroleum feedstock.

28. The process of claim 27, wherein at least about 80 wt. % of the mixture of $C_3$-$C_6$ alcohols is derived from a non-petroleum feedstock.

29. The process of claim 28, wherein at least about 90 wt. % of the mixture of $C_3$-$C_6$ alcohols is derived from a non-petroleum feedstock.

30. The process of claim 29, wherein at least about 95 wt. % of the mixture of $C_3$-$C_6$ alcohols is derived from a non-petroleum feedstock.

31. The process of claim 1, wherein a portion of the mixture of $C_3$-$C_6$ alcohols is produced in an alcohol biorefinery via fermentation of sugars by yeast.

32. The process of claim 31, wherein the alcohol biorefinery is an ethanol production plant.

33. The process of claim 1, wherein a portion of the mixture of $C_3$-$C_6$ alcohols is obtained from biomass-generated syngas.

34. The process of claim 33, wherein a second portion of the mixture of $C_3$-$C_6$ alcohols is obtained from syngas that has been derived from natural gas, coal, or a combination thereof.

35. The process of claim 1, wherein the reactor feed comprises water.

36. The process of claim 35, wherein the reactor feed comprises less than about 15 wt. % water.

37. The process of claim 36, wherein the reactor feed comprises greater than about 10 wt. % water.

38. The process of claim 37, wherein the reactor feed comprises greater than about 5 wt. % water.

39. The process of claim 1, wherein the reactor feed comprises ethanol.

40. The process of claim 39, wherein the ethanol is at a concentration of less than about 20 wt. %.

41. The process of claim 40, wherein the ethanol is at a concentration of greater than about 10 wt. %.

42. The process of claim 41, wherein the ethanol is at a concentration of greater than about 5 wt. %.

43. The process of claim 42, wherein the ethanol is at a concentration of greater than about 2 wt. %.

44. The process of claim 1, wherein the reactor feed comprises ethanol, water, and the $C_3$-$C_6$ alcohols.

45. The process of claim 1, wherein the mixture of $C_3$-$C_6$ alcohols includes at least one of 2-methyl-1-butanol (active amyl alcohol), isoamyl alcohol (isopentanol), isobutyl alcohol, and n-propyl alcohol, propanol, butanol, pentanol, or hexanol.

46. The process of claim 45, wherein the mixture of $C_3$-$C_6$ alcohols includes two or more of 2-methyl-1-butanol (active amyl alcohol), isoamyl alcohol (isopentanol), isobutyl alcohol, and n-propyl alcohol, propanol, butanol, pentanol, or hexanol.

47. The process of claim 1, wherein the mixture of $C_3$-$C_6$ alcohols is contacted with the mixed oxide catalyst at a temperature within the range of about 300° C. to about 600° C.

48. The process of claim 47, wherein mixture of $C_3$-$C_6$ alcohols is contacted with the mixed oxide catalyst at a temperature within the range of about 400° C. to about 500° C.

49. The process of claim 48, wherein the mixture of $C_3$-$C_6$ alcohols is contacted with the mixed oxide catalyst at a temperature within the range of about 415° C. to about 470° C.

50. The process of claim 49, wherein the mixture of $C_3$-$C_6$ alcohols is contacted with the mixed oxide catalyst at a temperature within the range of about 425° C. to about 445° C.

51. The process of claim 1, wherein the mixture of $C_3$-$C_6$ alcohols is contacted with the mixed oxide catalyst at a weight hourly space velocity range of about 0.1 $hr^{-1}$ to about 2.5 $hr^{-1}$.

52. The process of claim 51, wherein the mixture of $C_3$-$C_6$ alcohols is contacted with the mixed oxide catalyst at a weight hourly space velocity of about 2.0 $hr^{-1}$.

53. The process of claim 52, wherein the mixture of $C_3$-$C_6$ alcohols is contacted with the mixed oxide catalyst at a weight hourly space velocity of about 1.5 $hr^{-1}$.

54. The process of claim 1, wherein the mixed oxide catalyst is prepared using a hard-template method, a co-precipitation method, or an impregnated method.

55. The process of claim 1, wherein X is 0.

56. The process of claim 55, wherein the ratio of $Zn_v/Mg_w/Mn_y/Zr_z$ (V:W:Y:Z) in the mixed oxide catalyst is about 1:2:5:18.

57. The process of claim 55, wherein the ratio of $Zn_v/Mg_w/Mn_y/Zr_z$ (V:W:Y:Z) in the mixed oxide catalyst is about 1:4:5:18.

58. The process of claim 55, wherein the ratio of $Zn_v/Mg_w/Mn_y/Zr_z$ (V:W:Y:Z) in the mixed oxide catalyst is about 2:1:5:18.

59. The process of claim 55, wherein the ratio of $Zn_v/Mg_w/Mn_y/Zr_z$ (V:W:Y:Z) in the mixed oxide catalyst is about 2:2:5:18.

60. The process of claim 1, wherein the mixture of $C_3$-$C_6$ alcohols is obtained from a combination of biomass-generated syngas and syngas that has been derived from natural gas, coal, or a combination thereof.

61. The process of claim 1, wherein the ratio of $Zn_v/Mg_w/Mn_y/Zr_z$ (V:W:Y:Z) in the mixed oxide catalyst is about 0:0:5:18.

62. The process of claim 1, wherein the ratio of $Zn_v/Mg_w/Mn_y/Zr_z$ (V:W:Y:Z) in the mixed oxide catalyst is about 0:2:5:18.

63. The process of claim 1, wherein the ratio of $Zn_v/Mg_w/Mn_y/Zr_z$ (V:W:Y:Z) in the mixed oxide catalyst is about 1:0:5:18.

64. The process of claim 1, wherein the ratio of $Zn_v/Mg_w/Mn_y/Zr_z$ (V:W:Y:Z) in the mixed oxide catalyst is about 2:0:5:18.

65. A process for converting fusel oil comprising one or more $C_2$-$C_6$ linear or branched alcohols to a product comprising at least one of a ketone, an olefin, a di-olefin, or an aldehyde, comprising contacting the fusel oil with a mixed metal oxide manganese/zirconium catalyst, doped with an element selected from the group consisting of magnesium, zinc, copper, and combinations thereof.

66. The process of claim 65, wherein the one or more $C_2$-$C_6$ linear or branched alcohols comprise at least 50 wt. % of organic material within the fusel oil.

67. The process of claim 65, wherein the manganese/zirconium catalyst further comprises from about 0.01 wt. % to about 20 wt. % manganese and 35-70% zirconium.

68. The process of claim 65, wherein the manganese/zirconium catalyst further comprises from about 0.01 wt. % to about 10 wt. % magnesium and 0.01 wt. % to about 10 wt. % zinc, and 0.01 wt. % to about 10 wt. % copper, or combinations thereof.

69. A process for converting fusel oil comprising one or more $C_2$-$C_5$ linear or branched alcohols to a product comprising $C_5$ olefins, comprising contacting the fusel oil with a mixed γ-alumina catalyst, optionally doped with potassium.

70. The process of claim 69, wherein the $C_5$ olefins are at least one of 2-methyl-2-butene, 2-methyl-1-butene, and 3-methyl-1-butene.

71. A process for converting fusel oil comprising one or more $C_2$-$C_5$ linear or branched alcohols to a product comprising isoprene, comprising catalytically reacting the fusel oil with a zinc oxide catalyst to provide an intermediate comprising one or more $C_5$ aldehydes, then reacting the intermediate with a mixed acidic ZSM-5 zeolite catalyst doped with boron and phosphorus to provide the product comprising isoprene.

* * * * *